United States Patent
Herran Planchuelo et al.

(10) Patent No.: US 11,908,582 B2
(45) Date of Patent: Feb. 20, 2024

(54) ASSESSING THE FUNCTIONAL PERFORMANCE OF AN INDIVIDUAL

(71) Applicant: ADMINISTRACIÓN GENERAL DE LA COMUNIDAD AUTÓNOMA DE EUSKADI, Vitoria-Gasteiz (ES)

(72) Inventors: Jaime Herran Planchuelo, Donostia-San Sebastián (ES); Larraitz Añorga Gomez, Donostia-San Sebastián (ES); Itziar Vergara Micheltorena, Donostia-San Sebastián (ES); Kalliopi Vrotsou, Donostia-San Sebastián (ES); Marcos Jesus Arauzo Bravo, Donostia-San Sebastián (ES); Ander Matheu Fernández, Donostia-San Sebastián (ES)

(73) Assignee: ADMINISTRACIÓN GENERAL DE LA COMUNIDAD AUTÓNOMA DE EUSKADI, Vitoria-Gasteiz (ES)

( * ) Notice: Subject to any disclaimer, the term of this patent is extended or adjusted under 35 U.S.C. 154(b) by 305 days.

(21) Appl. No.: 17/416,400

(22) PCT Filed: Dec. 19, 2019

(86) PCT No.: PCT/EP2019/086277
§ 371 (c)(1),
(2) Date: Jun. 18, 2021

(87) PCT Pub. No.: WO2020/127709
PCT Pub. Date: Jun. 25, 2020

(65) Prior Publication Data
US 2022/0059233 A1    Feb. 24, 2022

(30) Foreign Application Priority Data
Dec. 21, 2018 (EP) .................... 18382973

(51) Int. Cl.
*G16H 50/30* (2018.01)
*A61B 5/11* (2006.01)
*A61B 5/00* (2006.01)

(52) U.S. Cl.
CPC .......... *G16H 50/30* (2018.01); *A61B 5/1114* (2013.01); *A61B 5/1118* (2013.01); *A61B 5/7257* (2013.01);
(Continued)

(58) Field of Classification Search
CPC .......... G16H 50/00; G16H 50/30; A61B 5/11; A61B 5/103; A61B 5/1114; A61B 5/1118
(Continued)

(56) References Cited

U.S. PATENT DOCUMENTS

| 9,165,113 | B2 | 10/2015 | Greene et al. |
| 9,676,098 | B2* | 6/2017 | Hemken ............... B25J 9/163 |
| 11,253,173 | B1* | 2/2022 | Demiralp ............ A61B 5/1122 |

FOREIGN PATENT DOCUMENTS

| EP | 1912051 A2 | 4/2008 |
| PT | 107553 A | 9/2015 |

OTHER PUBLICATIONS

International Search Report and Written Opinion dated Mar. 11, 2020 for Application No. PCT/EP2019/086277, 15 pages.
(Continued)

*Primary Examiner* — Hai L Nguyen
(74) *Attorney, Agent, or Firm* — SQUIRE PATTON BOGGS (US) LLP

(57) ABSTRACT

The description relates to a system for assessing the functional performance of an individual, the system comprising a sensor device; a monitoring system, connectable to the sensor device, configured to receive signals coming from the sensor device, pre-process the signals received from the sensor device, extract the main features of the pre-processed
(Continued)

signals to be used as predictor variables, assess the functional performance of an individual based on the predictor variables.

14 Claims, 13 Drawing Sheets

(52) U.S. Cl.
CPC . *A61B 2562/0219* (2013.01); *A61B 2562/046* (2013.01)

(58) Field of Classification Search
USPC .................................................. 73/488, 489
See application file for complete search history.

(56) References Cited

OTHER PUBLICATIONS

International Preliminary Report on Patentability dated Nov. 4, 2020 for Application No. PCT/EP2019/086277, 20 pages.

* cited by examiner

FIG.3
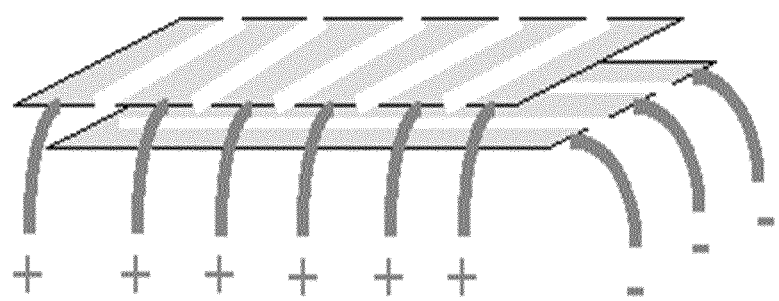
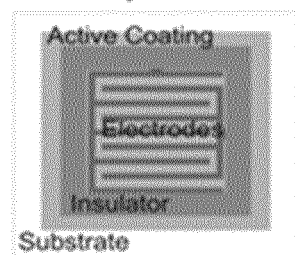
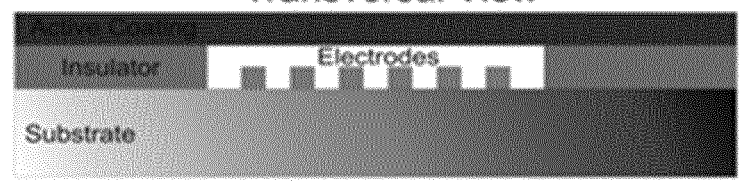
FIG.4

TUG confusion matrix

| TUG predicted | Robust | Fragile | |
|---|---|---|---|
| Robust | 38 / 81.8% | 0 / 0.0% | 100% / 100% |
| Fragile | 0 / 0.0% | 8 / 18.2% | 100% / 0.0% |
| | 100% / 0.0% | 100% / 0.0% | 100% / 0.0% |
| | Robust | Fragile | |

TUG measured

ASSESSING THE FUNCTIONAL PERFORMANCE OF AN INDIVIDUAL

CROSS-REFERENCE TO RELATED APPLICATIONS

This application is a national-stage filing under 37 USC 371(c) of International Application No. PCT/EP2019/086277, filed Dec. 19, 2019, which claims priority to, and the benefit of, European Patent Application 18382973.8, filed Dec. 12, 2018. The entire contents of each of these applications are herein incorporated by reference in their entirety for all purposes.

The present disclosure relates to systems for assessing the functional performance of an individual such as systems for identifying the state of fragility or robustness of the individual or systems for identifying individuals with high risk of fractures and other health related adverse outcomes.

BACKGROUND

Nowadays, systems for assessing the functional performance of an individual are known.

The assessment of functional performance is recommended by WHO in aged populations in order to categorize them and define, accordingly to this categorization, the therapeutical objectives to be achieved. Low functional performance is associated with the status of frailty and with an increased risk of presenting hip fractures and other health related adverse events.

Frailty is a clinical syndrome characterised by increased vulnerability to low intensity stressors. Frail elderly individuals have a reduced functional performance capacity. They are independent in their basic daily life activities but have a greater risk of becoming dependent as a consequence of a minor event, such as a respiratory or urinary tract infection, for example. The pathophysiological origin of this syndrome resides in the alteration of numerous interrelated systems (immune, endocrine, musculoskeletal, and neurological systems, and so forth) which lead to a decreased homeostatic reserve and decreased adaptive capacity for the individual, which predisposes them to adverse health events. Frailty has been shown to be an independent risk factor for serious adverse health effects, such as institutionalisation, hospitalisation, falls, disability and dependency. Frail individuals have a six times greater risk of becoming dependent than healthy individuals of their same age and sex. Its prevalence varies according to the measurement instrument used and the scope of the study, but it oscillates between 15 and 25% of the population over 70 years old.

The most widely used tests to assess functional performance are: Gait speed (GS) the Timed Up and Go (TUG) Test and Short Physical Performance Battery (SPPB). These performance tests are considered to be sufficient in identifying frail subjects and in identifying subjects with high risk of presenting hip fractures and other health related adverse events.

Gait speed test measures the time an individual needs to walk a predefined distance. Different versions exist based on distances of 4, 6, 8 and 10 m.

The TUG test involves measuring the time it takes for the elderly individual to get up from a chair, walk 3 metres, turn around, return to the chair and sit down again. The outcome is considered normal if the individual performs this activity in 12 seconds or less, even though other cut points have been proposed for various purposes.

The SPPB, on the other hand, assesses a battery of functional tests including walking speed, the ability to get up from a chair repeatedly and balance.

All tests are performed in person with a trained evaluator, a chair, distance marks on the floor and a stopwatch to measure the times needed to perform the test. These features (the spatial characteristics, the chair, the professional's messages and attitude, and so forth) lead to high variability in the test results in addition to the inconveniences related with the space and time required to apply the test.

In recent years, devices have been developed to measure the functional capacity, specifically the walking speed, balance and acceleration. These devices are based on portable sensors (walking speed, centre of gravity, and inertia), pressure sensors on the carpets (walking speed, centre of gravity, and strength), gyroscopes, cameras and acceleration sensors, among others. Certain proposals based on acceleration have currently been identified as an alternative to the traditional measurement procedure for the process of sitting and getting up from a chair.

U.S. Pat. No. 9,165,113 discloses methods, systems, and apparatus for quantifying an individual's frailty level based on inertial sensor data collected from the individual.

Consequently, there is a need for a system that at least partially solves the aforementioned problems.

SUMMARY

In a first aspect, a system for assessing the functional performance of an individual is provided. The system may comprise:
  a sensor device;
  a monitoring system, connectable to the sensor device, configured to:
    receive signals coming from the sensor device;
    pre-process the signals received from the sensor device;
    extract the main features of the pre-processed signals to be used as predictor variables;
    assess the functional performance of an individual based on the predictor variables.

This way, the provision of the sensor device and the disclosed monitoring system allows assessing the functional performance of an individual based on the study of the individual dynamics of sitting, that is, only analysing the process of sitting down and standing up performed by the individual is enough for assessing his/her functional performance. This is so because the reduction of a person's functional performance, beyond affecting the total execution time of certain exercises, also affects the dynamics of the movement of sitting down and standing up, for example, from a seat. The stability, the force (pressure) and the kinematics used by an individual are different according to their functional performance. The system of the invention is capable of registering, in real time, said dynamics by the sensor device and process it by the monitoring system and assessing the functional performance of the individual. Consequently, complex exercises are no longer required and variability in the result is avoided.

The sensor device may comprise an array of sensors. More specifically, the sensor device may be based on distributed pressure sensors, such as flexible pressure sensors, for example, large surface distributed pressure sensors.

According to some examples, the sensor device may comprise an array of sensors of $N_r \times N_c$ that produces a $N_r \times N_c$ measurement matrix for each sampling time. The received signals may be in the form of a tri-dimensional tensor $T_S$ of order $N_r \times N_c \times N_S$, where $N_r$ is the number of rows of the array of sensors, $N_c$ is the number of columns of the array of sensors, and $N_S$ is the number of sampling times.

In this case, pre-processing, by the monitoring system, the signals received from the sensor device may comprise:

producing an equi-order tensor $T_{MAX}$ of dimensions $N_r \times N_c \times N_{MAX}$;

vectoring the produced equi-order tensor $T_{MAX}$ into a vector V of length $N_{MAX}$, in which to each position i in [1 $N_{MAX}$] is assigned the sum of the elements of the $N_r \times N_c$ measurement matrix in the position i of the tensor $T_{MAX}$.

Step of pre-processing allows adapting the signals coming from the sensor device and preparing them to be processed by the downstream modules (i.e. to be digested by the rest of modules of the monitoring system).

In some examples, producing, by the monitoring system, an equi-order tensor $T_{MAX}$ of dimensions $N_r \times N_c \times N_{MAX}$ may comprise:

reformatting the tri-dimensional tensor $T_S$ of order $N_r \times N_c \times N_S$ according to:
if $N_S \geq N_{MAX}$, truncating the third dimension of the tensor $T_S$ to the length $N_{MAX}$, transforming the tensor $T_S$ into a tensor $T_{MAX}$ of dimensions $N_r \times N_c \times N_{MAX}$;
if $N_S \leq N_{MAX}$, padding the third dimension of the tensor $T_S$ to the length $N_{MAX}$, transforming the tensor $T_S$ into a tensor $T_{MAX}$ of dimensions $N_r \times N_c \times N_{MAX}$;
if $N_S = N_{MAX}$, renaming $T_S$ as $T_{MAX}$.

In some examples, padding, by the monitoring system, the third dimension of the tensor $T_S$ to the length $N_{MAX}$, if $N_S \leq N_{MAX}$, may comprise attaching after the tensor $T_S$ of order $N_r \times N_c \times N_S$ a padding tensor $T_p$ of dimensions $N_r \times N_c \times N_p$, where $N_p$ is the padding length $N_p = N_{MAX} - N_S$.

According to some examples, pre-processing, by the monitoring system, the signals received from the sensor device may comprises correcting the background of the vector V for obtaining a background corrected vector $V_b$.

In some examples, correcting, by the monitoring system, the background of the vector V may comprise subtracting from each element of vector V the value of the minimum element of V, $V_{MIN}$, such that a background corrected vector $V_b$ is obtained.

In some examples, extracting, by the monitoring system, the main features of the pre-processed signals to be used as predictor variables, predictor variables being signal descriptive variables in the time domain, may comprises obtaining the signal descriptive variables in the time domain vector $V^{DESCRIPTIVE}$.

Step of extracting the main features of the pre-processed signals allows summarizing the vector $V_b$ signal in a compact way to be more easily processed by the downstream modules. The vector $V_b$ has a variable length and its signal behaves in a noise complicated way. These two features make this vector difficult for manipulation by the downstream modules. The transformation of this vector to a collection of descriptive variables with fixed dimensions and robust to the noise solves the aforementioned drawbacks.

In some examples, signal descriptive variables in the time domain may be selected from at least one of the following:
Range of variation of the signal;
Instant of the maximum peak of the signal;
Standard deviation of the signal;
Slope of the signal defined as the ratio between the range and the instant of the maximum peak;
Start time of change of the signal;
Integral of the signal.

In some examples, extracting, by the monitoring system, the main features of the pre-processed signals to be used as predictor variables, predictor variables being signal time series variables in the time domain, may comprise:

filtering the noise of the background corrected vector $V_b$ with a smoothing moving window;

reducing the sample length of the filtered vector $V_b$ by decimation factor of d, such that the signal time series variables in the time domain vector $V^{TIME}$ is obtained.

According to some examples, reducing, by the monitoring system, the sample length of the filtered vector $V_b$ by decimation factor of d may comprise at least of the following:

applying a simple resampling of $V_b$ each time d;

applying a lowpass Chebyshev Type I Infinite Impulse Response (IIR) filter;

applying a Finite Impulse Response (FIR) filter with a Hamming window.

In some examples, extracting, by the monitoring system, the main features of the pre-processed signals to be used as predictor variables, predictor variables being signal spectral variables in the frequency domain, may comprise:

truncating the background corrected vector $V_b$ length to the floor operator $L_T$ of maximum power of 2 of the length of the vector $V_b$;

applying a Fast Fourier transform to the truncated vector $V_b$ using a Discrete Fast Fourier method;

obtaining the spectral power P of the vector $V_b$ based on the result of applying the Fast Fourier transform to the truncated vector $V_b$;

truncating the obtained spectral power vector, such that the signal spectral variables in the frequency domain vector $V^{FREQUENCY}$ is obtained.

In some examples, extracting, by the monitoring system, the main features of the pre-processed signals to be used as predictor variables may comprise:

obtaining the respective maximum and minimum values of the obtained predictor variables;

normalizing, based on the obtained maximum and minimum values, between 0 and 1, the obtained predictor variables;

attaching in a vector $V^P$ the normalized predictor variables $V^{DESCRIPTIVE}$, $V^{TIME}$ and $V^{FREQUENCY}$.

In some examples, the monitoring system may be configured to:

detect whether any of the received signals coming from the sensor device is wrong.

Step of detecting whether any of the received signals coming from the sensor device is wrong allows detecting whether the sensor device is producing wrong measurements. These wrong measurements may be due to wrong manipulations by the individual using the sensor device or by hardware failures. Consequently, this action is convenient for troubleshooting. If the individual using the sensor device proceeds correctly following the instructions and there are no hardware problems, warning signals will not be generated. However, in the event of any manipulation error or hardware damage, a warning signal that will help avoid downstream problems will be generated.

According to some examples, detecting, by the monitoring system, whether any of the received signals coming from each sensor of the array of sensors is wrong may comprise:

rejecting a received signal if at least one of the following conditions are fulfilled:

the length of the recorded sample is shorter than $N_S$;
the maximum of the signal across the recording period is less than a predetermined threshold $\theta_{MAX}$.

In some examples, detecting, by the monitoring system, whether any of the received signals coming from each sensor of the array of sensors is wrong may comprise, if a received signal is rejected, generating a warning about the rejection of the signal.

A warning may be generated, for example, by at least one of the following actuator elements:
- at least one actuator element configured to generate an audible signal (e.g. a speaker, a buzzer, etc.);
- at least one actuator element configured to generate a visual signal (e.g. a display screen (for example, LCD), a plurality of LEDs (Light Emitting Diode), etc.);
- at least one actuator element configured to generate a haptic signal (e.g. a vibrator motor).

In some examples, assessing, by the monitoring system, the functional performance of an individual based on the extracted predictor variables may comprise:
- predicting the value of the TUG (Timed Up Go) test of the individual based on the extracted predictor variables $V_P$;
- assessing the functional performance of an individual based on the predicted value of the TUG test.

Step of predicting the value of TUG test uses as independent variables the obtained predictor variables.

In some examples, predicting, by the monitoring system, the value of the TUG (Timed Up Go) test of the individual based on the extracted predictor variables may comprise:
- applying a regression method taking into account the extracted predictor variables $V^P$;
- rescaling the output of the regression method to obtain the final prediction of TUG.

In some examples, the regression method may be selected from at least one of the following:
- linear regression method such as a multiple linear regression method with the least square optimization;
- a robust fit method using a weight function w( );
- a non-linear regression method such as quadratic polynomial piecewise linear
- interpolation smoothing splines;
- local linear regression method.

On the other hand, the robust fit method using a weight function w( ) may comprise at least one of the following:
- Andrews function w=(abs(k)<π) sin(k)/k
- Bisquare function w=(abs(k)<1) (1−k2)2
- Cauchy function w=1/(1+k2)
- Fair function w=1/(1+abs(k))
- Huber function w=1/max(1, abs(k))
- Logistic function w=tan h(k)/k
- Talwar function w=(abs(k)<1)
- Welsch function w=exp(−(k2))

where k is a parameter.

In some examples, assessing, by the monitoring system, the functional performance of an individual based on the extracted predictor variables may comprise:
- identifying the state of fragility or robustness of the individual based on the extracted predictor variables $V^P$.

This way, an individual may be classified as fragile or robust.

According to some examples, identifying, by the monitoring system, the state of fragility or robustness of the individual based on the extracted predictor variables may comprise:
- using an Artificial Neural Network to predict the state of fragility or robustness of the individual, the Artificial Neural Network having a topology of an input layer comprising as many neurons as predictor variables are obtained, at least one hidden layer with a predetermined number of neurons, an output layer with at least one neuron.

In some examples, the transfer function to calculate the output of each neuron of each layer may be selected from at least one of the following:
- Competitive transfer function;
- Elliot sigmoid transfer function;
- Positive hard limit transfer function;
- Symmetric hard limit transfer function;
- Logarithmic sigmoid transfer function;
- Inverse transfer function;
- Positive linear transfer function;
- Linear transfer function;
- Radial basis transfer function;
- Radial basis normalized transfer function;
- Positive saturating linear transfer function;
- Symmetric saturating linear transfer function;
- Soft max transfer function;
- Symmetric sigmoid transfer function;
- Triangular basis transfer function.

In some examples, the learning method may be selected from at least one of the following:
- Stochastic gradient descent with momentum (SDGM);
- Backpropagation methods such as the Broyden-Fletcher-Goldfarb-Shanno (BFGS) quasi-Newton backpropagation, conjugate gradient backpropagation with Powell-Beale, Fletcher-Reeves, or Polak-Ribiere restarts, the gradient descent backpropagation, the gradient descent with adaptive IR backpropagation, the gradient descent with momentum, the gradient descent w/momentum & adaptive IR backpropagation; the one step secant backpropagation, the resilient backpropagation (RPROP), the scaled conjugate gradient backpropagation.

According to some examples, assessing, by the monitoring system, the functional performance of an individual based on the extracted predictor variables may comprise:
- identifying individuals with high risk of fractures and other health related adverse outcomes based on the extracted predictor variables.

In some examples, identifying, by the monitoring system, individuals with high risk of fractures and other health related adverse outcomes based on the extracted predictor variables may comprise:
- predicting the value of the TUG (Timed Up Go) test of the individual based on the extracted predictor variables $V^P$;
- identifying individuals with high risk of fractures and other health related adverse outcomes based on the predicted value of the TUG test.

In another aspect, a non-transitory computer program product that causes a monitoring system to perform the steps executed by the monitoring system as described above. The computer program product may comprise program instructions that may be embodied on a storage medium (for example, a CD-ROM, a DVD, a USB drive, on a computer memory or on a read-only memory) or carried on a carrier signal (for example, on an electrical or optical carrier signal).

In yet another aspect, a computer-readable medium having thereon computer-executable instructions, the computer-executable instructions upon execution configuring a monitoring system to perform the steps executed by the monitoring system as described above.

BRIEF DESCRIPTION OF THE DRAWINGS

Non-limiting examples of the present disclosure will be described in the following, with reference to the appended drawings, in which:

FIG. 3 shows a schematic diagram of the symmetric configuration of a pressure sensor according to some examples in which the white lines represent nonconductive insulating spacers separating polythiophene conductive tracks;

FIG. 4 shows a schematic diagram of a sensor array with a top and a transversal view;

FIG. 13 shows a confusion matrix, in which the rows correspond to the predicted class (predicted TUG) and the columns correspond to the measured class (measured TUG);

DETAILED DESCRIPTION OF EXAMPLES

Figure 1:
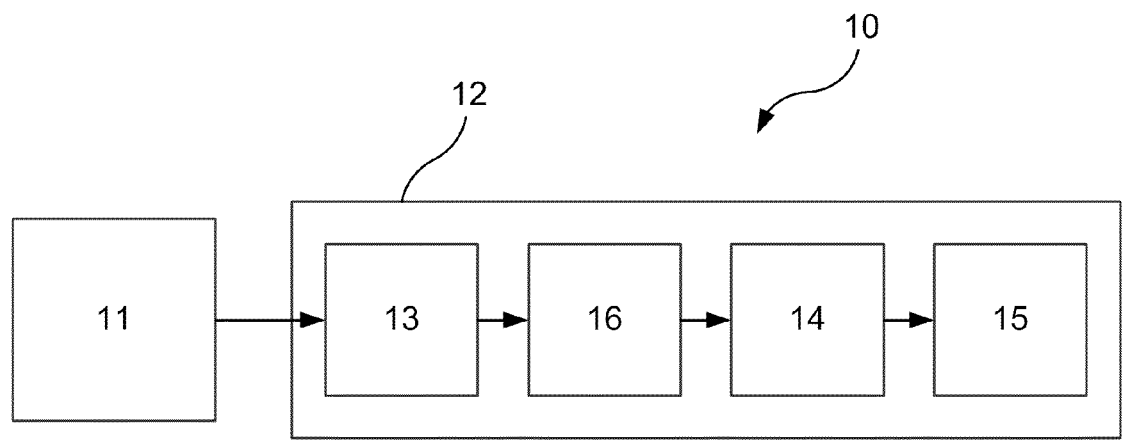
FIG. 1 is an illustration of a block diagram describing an example of a system for identifying the state of fragility or robustness of an individual, according to some examples.

As can be seen in FIG. 1, a system 10 assessing the functional performance of an individual may comprise:
a sensor device 11;
a monitoring system 12, connectable to the sensor device 11.

Said assessing system 10 may be understood as an interface between the sensor device 11 and, for example, a Graphical User Interface application (GUI) (not shown) configured to show, for example, the results.

In some examples, the sensor device 11 may be based on distributed pressure sensors, such as flexible pressure sensors. More specifically, distributed pressure sensors may be useful to determine strength or pressure upon soft objects, e.g., to measure the interface pressures of a person sitting on a chair. For this application it may be necessary for the sensor device 11 to be flexible in order to adjust, for example, to the shape of a seat or floor curvature and to adequately measure the forces exerted. Moreover, the sensor must be thin enough as to not introduce reading errors. This type of sensor usually has a thickness comprised between 0.1 and a few millimetres. In order to measure pressure at different points on a surface, it is necessary that the sensor area of each element in the distributed sensor is as small as possible. In general, according to the number of sensor elements used, these are classified into: single sensors and sensor arrays of n×m elements (where n and m may be equal, that is, n=m). These can in turn be classified according to output signals into two (on-off) or more output sensors (analogue or digital sensors).

The performance required from flexible pressure sensors is usually less than that required from conventional rigid sensors, with measurement inaccuracies of between 5 and 10% being accepted. Flexible pressure sensors are usually made up of a series of rows and columns in matrix-type arrangements. Flexible pressure sensors of n×m sensor elements provide data on pressure distribution on n×m areas ($n^2$ if n=m) of the sensor. This data is collected in the form of an electronic signal by converting the measurement of the change in resistance/capacitance/inductance provided by the sensor element into voltage or intensity. The data thus obtained may be linearized in order to optimize its resolution and simplify its interpretation. In order to increase measurement precision, the different sensor elements are calibrated by adjusting the corresponding gains and offsets or by establishing calibration curves. Data treated in this way allows generating two- and three-dimensional pressure maps in real time.

Amongst the different technologies that exist for developing distributed pressure sensors it is possible to mention: the technology using piezoelectric elements, and pneumatic, hydraulic, resistive, capacitive or inductive technologies. Piezoelectric technology cannot be used for static measurements due to current loss in these sensors, which makes the response signal tend towards zero with time. Sensors based on pneumatic and hydraulic technologies require very complicated assemblies and large thicknesses, which limits their application in flexible sensors. Nowadays, consequently, resistive and capacitive technologies are the most used in flexible pressure sensors.

The operating principle of resistive sensors is based on the change in electric resistance that takes place in piezoresistive materials when a force or pressure is applied upon them. In the case of capacitive sensors, these are based on the change in capacitance that occurs between two parallel plates between which there is a nonconductive elastomeric material, when a force or pressure is applied upon them. This last type of sensor has the drawback of requiring very precise and highly sensitive and stable electronics, since the changes in capacitance measured are usually less than pico faradays. In contrast, resistive-type flexible pressure sensors use very simple electronics, since changes in resistance are of several orders of magnitude and fast, which is important for arrays of many sensor elements, and hardly sensitive to electromagnetic fields (another drawback of capacitive sensors). Amongst the disadvantages of these sensors we can highlight their non-linearity and the dependence of their response to the number of cycles and the history of the sensor. Moreover, the response of these sensors usually depends on temperature and the degree of relative humidity, and they can thus show low signal stability and a lifetime that is not sufficiently long.

The disclosed drawbacks may be solved, for example, by large surface distributed pressure sensors comprising at least two flexible substrates, at least one of these being entirely or partially coated by a layer of polythiophene (or any other semiconductor material or any other material with an average conductivity), and one or more insulating spacers.

The term "large surface distributed pressure sensor" may refer to a sensor that is capable of providing pressure measurements over a large surface (greater than 1 cm×1 cm) which may in turn be curved and flexible, in contrast to point pressure sensors.

This way, for example, Polythiophene-based sensors are described in EP1912051, whose title is "Polythiophene-based distributed pressure sensors having a large surface area". This application discloses that the layer of polythiophene may contain repetitive structural units with formula (I),

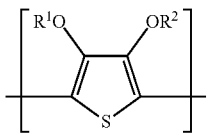

wherein $R^1$ and $R^2$ are independently a $C_1$-$C_{12}$ alkyl group or they form a $C_1$-$C_{12}$ 1, n-alkylene group, with n=1-12, optionally substituted by a $C_1$-$C_{12}$ alkyl group, $C_2$-$C_{12}$ alkene, vinylene, benzyl, phenyl group, a halogen atom, or by an ester, amine, amide or ether functional group, optionally substituted by a $C_1$-$C_{12}$ alkyl group.

A completely novel aspect according to EP1912051 is the use of the polythiophenes described above as sensor elements. Thus, according to some examples of the sensor, groups $R^1$ and $R^2$ of the polythiophene form an alkylene group chosen from methylene, 1,2-ethylene and 1,3-propylene. In some examples, said groups $R^1$ and $R^2$ form a 1,2-ethylene group, i.e. a polythiophene for the sensor may be poly(ethylene-dioxy-thiophene).

In some examples, the flexible substrate may be a flexible plastic sheet. The flexible plastic sheet may be made up of high polymers with a high melting point or a high glass transition temperature polymers, such as polyethylene terephthalate or polycarbonate.

In some examples, the flexible plastic sheet may be made of plasticized PVC, thermoplastic rubbers, fibres or polymer fabrics. On the other hand, the flexible substrate may be a sheet of a non-plastic material. In some examples, the flexible substrate may be a sheet of a cellulose derivative material, such as a sheet of cellulose paper. The flexible substrate may also be a sheet of a textile material and/or a sheet of flexible glass.

It has been found that when two flexible sheets coated with the disclosed polythiophenes come into contact such that both conductive films approach one another (using adequate insulating spacers) and a potential difference is established between them, the electric current passing through is directly proportional to the pressure exerted upon the sheets in a given range of pressures until, at very high pressures, the electric current saturates into a constant value.

Figure 2:
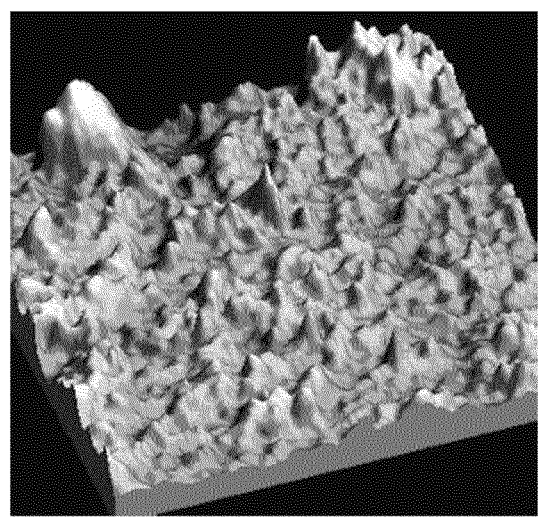
FIG. 2 shows an atomic force microscopy (AFM) photograph of the surface of a polythiophene-type conductive polymer and a graph of micro-roughness statistics.
Figure 2:
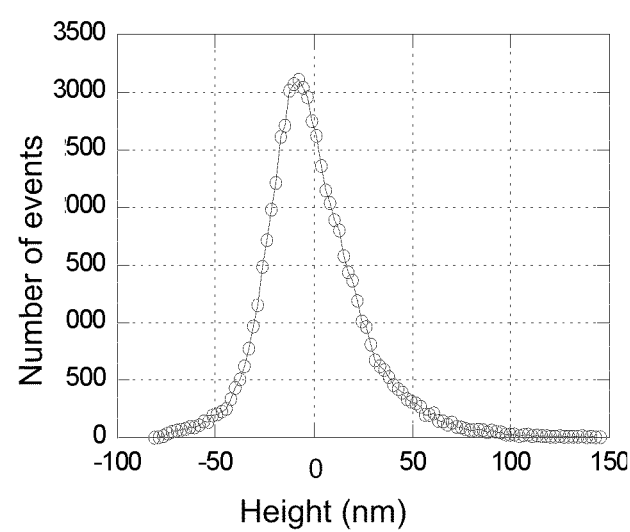

This effect, which is used for the manufacture of distributed pressure sensors based on the disclosed polythiophenes, could be attributed to the rough (and at the same time viscoelastic) nature, at the nanometre level, of the conductive films used, as shown in FIG. 2, performed by atomic force microscopy (AFM). Said morphology would include conductive particles (electron conductivity) of the polythiophene together with relatively insulating areas of a polyanion used as a dopant, as described below. Thus, it is possible to think that when the pressure upon the polythiophene-coated sheets increases the number of conductive contact points, at a nanometre scale, will increase until a certain pressure at which the maximum possible number of contact points is reached, and therefore, the value of the electric current becomes saturated. When the pressure is withdrawn, due to the viscoelastic nature of the material, it would return to approximately the original state in the absence of pressure.

In order to prevent short-circuits (in the absence of pressure) it may be convenient to use insulating spacers when assembling the distributed pressure sensors, as well as to adjust the pressure range in which the sensors respond within linearity. Said spacers may be made in materials of a suitable elastic module to cover a determined range of pressures such that the range of pressure the sensor is capable of detecting can be controlled according to its thickness and viscoelastic properties. In some examples, the insulating spacer may be a silicone, a polymeric foam or an epoxy resin.

As has been mentioned, said polythiophenes in their oxidised state may additionally incorporate anionic groups that stabilise the delocalised positive charge carriers in the polymer chains. This way, in some examples, the polythiophene may incorporate an anionic dopant. Said anionic dopant may be an inorganic anion, preferably a sulphate, chloride or bromide anion. In addition, said anionic dopant may be an organic anion with sulphonate or phosphate groups, preferably a p-toluene-sulphonic or p-toluene-phosphonic acid or said anionic dopant may be an organic polyanion chosen from polymeric carboxylic acids, preferably poly(acrylic acid), poly(methacrylic acid) or poly(maleic acid); polymeric sulphonic acids, preferably poly(styrene sulphonic) acid or poly(vinyl sulphonic) acid; or copolymers of vinyl carboxylic and vinyl sulphonic acids with other polymerizable monomers, such as styrene and acrylic or methacrylic monomers. In some examples, the molecular weight of said polyanions may be comprised, preferably, between 15,000 and 300,000 Daltons.

With respect to possible configurations, the simplest one is the symmetric configuration formed by two identical flexible sheets on which the polythiophene conductive tracks have been deposited, separated regularly by insulating spacers, and which are placed perpendicularly between them. In this case, the height of said spacers must be greater than that of the polythiophene conductive tracks. As indicated above, the nonconductive insulating spacers have the function of preventing electric contact between the conductive tracks of both sheets, once these have been assembled sandwich-like, and optionally encapsulated, in the absence of pressure, when a current intensity is applied between the top and bottom sheets, as shown in FIG. 3.

The pressure sensor thus constructed provides an electric signal that is proportional to the pressure applied and its matrix arrangement (n rows×m columns) allows obtaining pressure distribution data on n×m (or $n^2$ if n=m) areas of the sensor. Moreover, the range of pressure it is capable of detecting can be modified depending on the viscoelastic properties of the spacer used.

A variant of the previous configuration is the substitution of one of the sheets containing polythiophene conductive tracks with conductive tracks made from the deposition of any other conductive material. Thus, according to some examples, it shows a simple configuration formed by a flexible sheet on which polythiophene conductive tracks have been deposited, separated regularly with insulating spacers, and a nonconductive flexible sheet on which tracks have been deposited of another conductive material which, in some examples, form two electrodes.

The term "conductive material" refers to a metal material (silver, copper, nickel, etc.) of the type conductive silver paste, graphite paste, copper, or an intrinsic conductive polymer of the type polypyrrole, polyaniline or polythiophene deposited from a solution or a dispersion.

Other configurations are those using sheets with a homogenous deposition of polythiophenes (a film, for example) upon them.

This way, in some examples, the sensor may have a three-layer configuration formed by a flexible sheet upon which a homogeneous conductive layer of polythiophene is deposited, a nonconductive flexible sheet upon which tracks of a conductive material have been deposited and a deposition of an insulating spacer upon the conductive sheet of polythiophene.

In some examples, the sensor may have a three-layer configuration formed by a flexible sheet upon which a homogeneous conductive layer of polythiophene is deposited, a nonconductive flexible sheet upon which tracks of a conductive material have been deposited and a deposition of an insulating spacer upon the nonconductive sheet with tracks of conductive material.

Said configurations have a multilayer structure formed by a sheet with a homogenous deposition of polythiophenes, a non-homogeneous electric insulating layer or insulating spacer and a sheet with conductive tracks performed from the deposition of any conductive material which, in particular, can form two electrodes. The electric insulating layer may be performed by the deposition of any nonconductive material or of high electric resistance upon any of the other layers and it can have different configurations, thicknesses and viscoelastic coefficients that allow the adaptation and optimisation of the measurement range of the sensor, according to that described above.

EP1912051 also discloses a procedure for preparing a large surface distributed pressure sensor according to that described above, wherein the polythiophene is totally or partially deposited upon the flexible substrate, in the form of a film or in the form of tracks, for example, as mentioned above.

The polythiophenes used may have film-forming capacity when applied from true solutions, colloidal dispersions or stable dispersions of finely divided particles, either aqueous or solvent-based, by oxidative polymerisation of the corresponding monomer or by in situ polymerisation methods upon the substrate such as those described in the reference [ADVANCED FUNCTIONAL MATERIALS 14, 615-622, 2004]. Amongst the preferred solvents are alcohols, methanol, ethanol and isopropanol, as well as mixtures of water with these alcohols or other water-miscible organic solvents such as acetone. Amongst the preferred oxidizing agents are ammonium persulphate, iron trichloride and iron tosylate. Additionally, polymeric binders of the type poly(vinyl alcohol), poly(vinyl acetate), etc. may be used and adhesion promoters of the type silanes, tackifying resins, etc. to facilitate the formation of highly adherent films upon the substrate.

Thus, in some examples, the polythiophene may be deposited as a film from true solutions, colloidal dispersions or stable dispersions of finely divided particles, either aqueous or solvent-based, by means of oxidative polymerisation of the corresponding polythiophene monomer. In some examples thereof a polymeric binder of the type poly(vinyl alcohol) or poly(vinyl acetate) and an adhesion promoter of the type silanes or tackifying resins may be used in order to facilitate the formation of a highly adherent film upon the flexible substrate.

According to some examples, the polythiophene may be deposited upon the flexible substrate as a film from true solutions, colloidal dispersions or stable dispersions of finely divided particles, either aqueous or solvent-based, by means of in situ polymerisation methods upon said substrate.

The forms of application upon flexible substrates may be by direct evaporation of the solvent once the dispersion or solution are extended thereon (painted), by immersion, spraying, spin-coating techniques, etc.

Thus, in some examples, the polythiophene solution or dispersion may be applied upon the flexible substrate by painting, immersion, spraying or spin-coating techniques, and subsequent direct evaporation of the solvent.

In some examples, the polythiophene may be deposited upon the flexible substrate as tracks using conventional methods of lithography, selective deposition of the conductive polymer as tracks by ink-jet printing or by stripping the conductive material from the flexible sheet by mechanical methods, preferably by milling.

According to some examples, the conductive tracks may form $2n$ electrodes corresponding to n sensors.

The previously described sensors may be illustrated with four examples, which in no case must be considered limiting of the scope thereof.

Example 1

Figure 5:
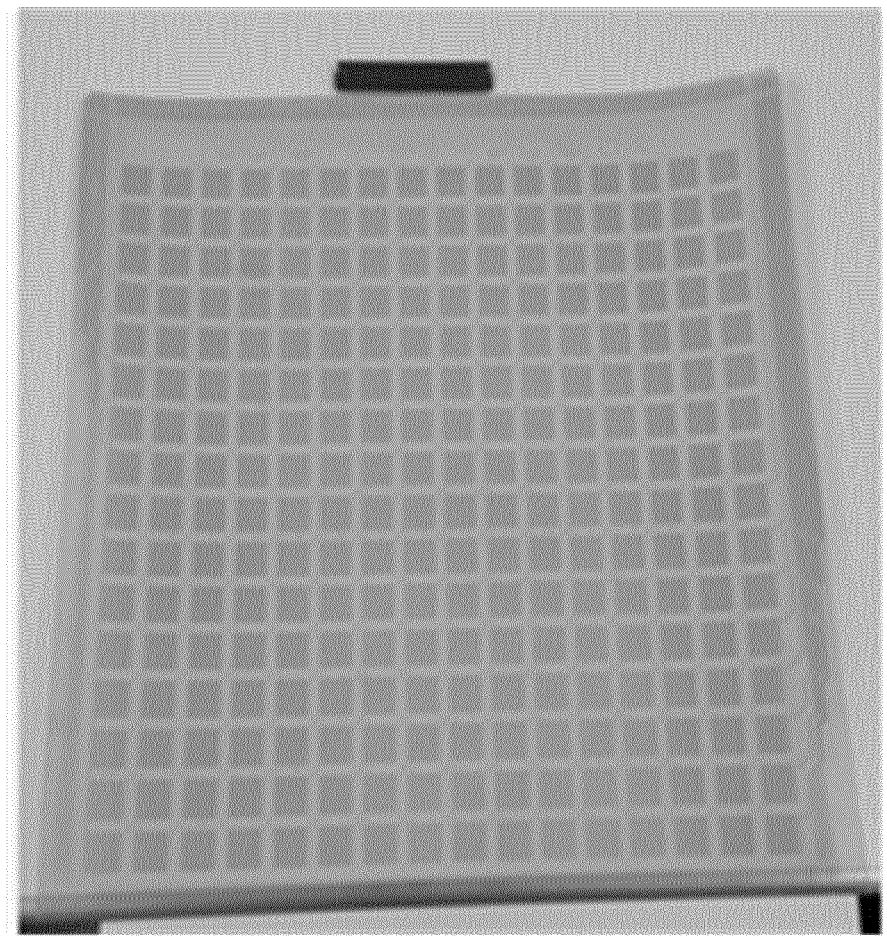
FIG. 5 shows a picture of the 16×16 sensor array (45×45 $cm^2$) of FIG. 4.

The pressure sensor sheet consists of a 256 analog sensor matrix, based on flexible printing electronics. The sensor configuration is formed by a 16×16 array with a spatial resolution of 2 cm² of tactile unit and a total area of 45×45 cm². Each single sensor is formed by silver interdigitated electrodes defined by screen-printing technology on a polyethylene terephthalate (PET) flexible substrate and a poly (3,4-dioxythyophene) (PEDOT) conducting polymer on the top side of the electrodes acting as an active coating. An insulating acrylate elastomeric coating is used as a separator between the electrodes and the electroactive coating. FIG. 4 shows a scheme of the sensor array (top and transversal view) and FIG. 5 shows a picture of the 16×16 sensor array (45×45 cm²).

Figure 6:
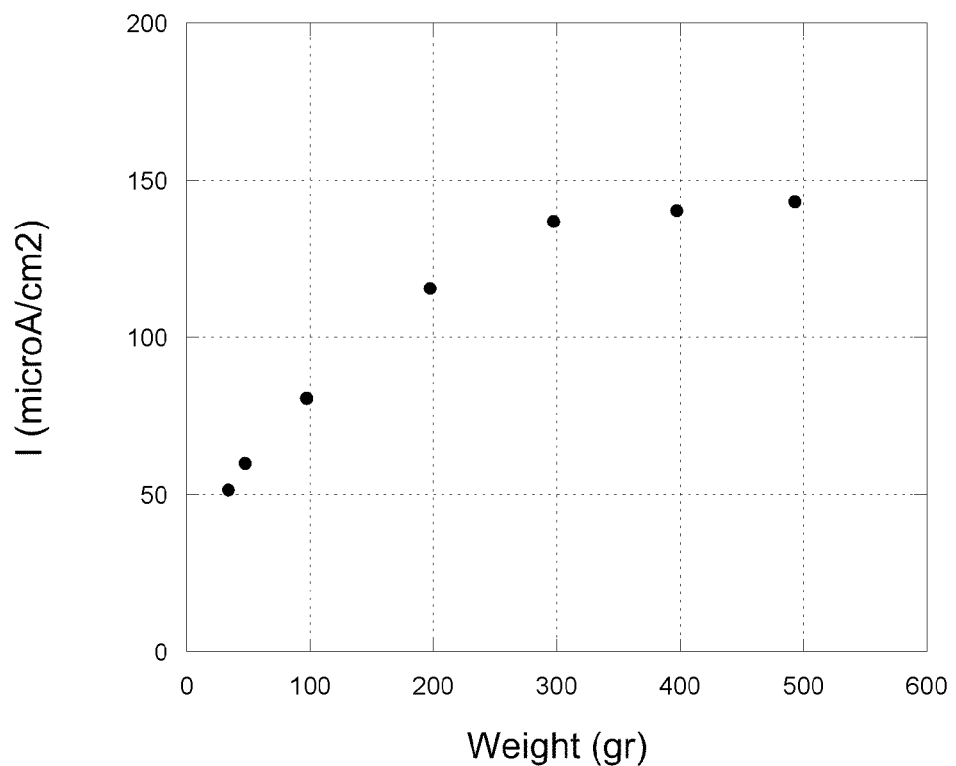
FIG. 6 shows a graph for the response in the form of current intensity for the symmetric configuration pressure sensor of the invention described in Example 2 versus the weight applied.

Example 2 (Preparation of a Pressure Sensor Based on a Symmetric Configuration of 5 Cm×5 cm of Active Area A pressure sensor was prepared from two flexible sheets of polyethylene terephthalate (PET) of 5 cm×5 cm of active area and 175 microns of thickness each, coated with a thin layer (1-2 microns) of poly(ethylene-dioxy-thiophene) containing as a polyanion a poly(styrene sulphonic) acid (PEDOT-PSS) deposited by oxidative polymerisation of the ethylene-dioxy-thiophene monomer in water, giving rise to a dispersion with a solid content of 2.5%. The sheets were assembled using an adhesive double-sided insulating spacer (IS) of 0.125 mm thickness in a symmetric sandwich-type configuration (PET/PEDOT-PSS/IS/PEDOT-PSS/PET), placing the spacer as a flat band 0.5 cm wide along the edges of the PEDOT-PSS-coated sheets. The pressure sensor thus assembled did not give any signs of current going through in the absence of pressure when a potential was applied between both sheets. Sensor response as current intensity measured when applying different weights upon the sensor surface and applying a potential difference of 1 V between both sheets is illustrated in FIG. 6.

Figure 7:
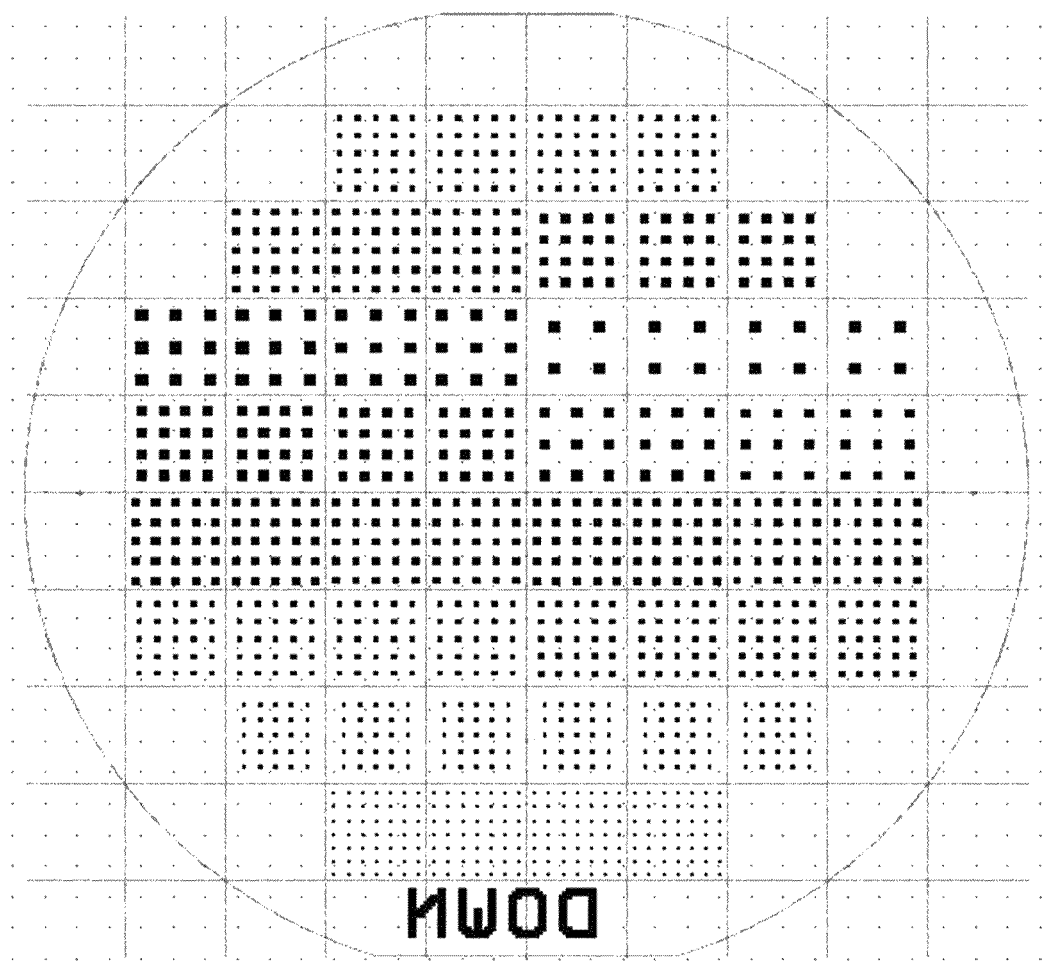
FIG. 7 represents different matrices of epoxy resin points that are useful for building the simple configuration pressure sensor of the invention described in Example 3.
Figure 8:
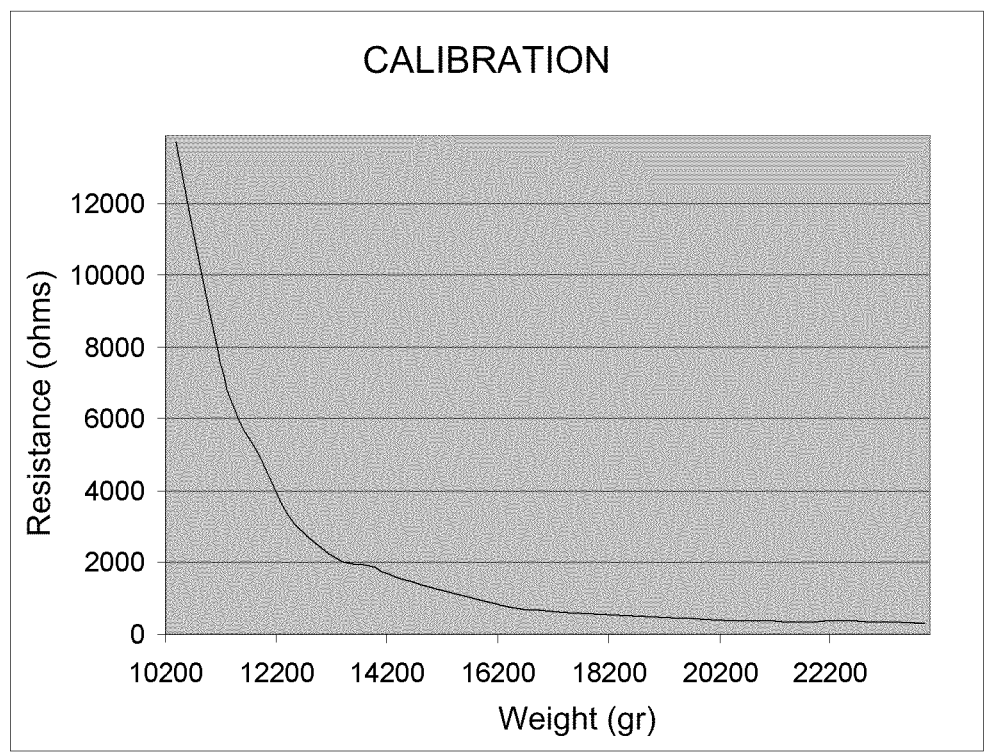
FIG. 8 shows a graph representing the change in resistance for the simple configuration pressure sensor described in Example 3 according to the weight applied.

Example 3 (Preparation of a Pressure Sensor Based on a Simple Configuration of 1 cm×1 cm of Active Area A pressure sensor was prepared from one flexible sheet of polyethylene terephthalate (PET) of 1 cm×1 cm of active area and 175 microns of thickness each, coated with a thin layer (1-2 microns) of poly(ethylene-dioxy-thiophene) containing as a polyanion a poly(styrene sulphonic) acid (PEDOT-PSS) deposited by oxidative polymerisation of the ethylene-dioxy-thiophene monomer in water, giving rise to a dispersion with a solid content of 2.5%. A matrix of points of epoxy resin was deposited upon this sheet with one of the configurations shown in FIG. 7 (thickness 15 microns). Another flexible sheet (polyester) upon which two electrodes of conductive material (silver) were deposited was adhered to the sample thus obtained. The assembled device showed very high electric resistance between the two electrodes (MΩs). The change in resistance of the sensor when applying different weights upon the surface thereof is illustrated in FIG. 8.

Example 4 (Preparation of a Pressure Sensor Based on a Symmetric Configuration of 5 Cm×5 cm of Active Area A pressure sensor was prepared from two flexible sheets of cellulose paper (CP) of 5 cm×5 cm of active area and 105 microns of thickness each, coated with a thin layer (1-2 microns) of poly(ethylene-dioxy-thiophene) containing as a polyanion a poly(styrene sulphonic) acid (PEDOT-PSS) deposited by oxidative polymerisation of the ethylene-dioxy-thiophene monomer in water, giving rise to a dispersion with a solid content of 2.5%. The sheets were assembled using an adhesive double-sided insulating spacer (IS) of 0.125 mm thickness in a symmetric sandwich-type configuration (CP/PEDOT-PSS/IS/PEDOT-PSS/CP), placing the spacer as a flat band 0.5 cm wide along the edges of the PEDOT-PSS-coated sheets. The pressure sensor thus assembled did not give any signs of current going through in the absence of pressure when a potential was applied between both sheets. Sensor response as current intensity measured when applying different weights upon the sensor surface and applying a potential difference of 1 V between both sheets was similar to that obtained by the sensor in Example 1.

In summary, the sensor device 11 may be based on distributed pressure sensors, such as flexible pressure sensors, for example, large surface distributed pressure sensors (e.g. polythiophene-based distributed pressure sensors) as described above.

The sensor device 11 may provide electrical or electronic signals to the monitoring system 12. This way, the sensor device 11 may be made up, for example, of a series of rows and columns in matrix-type arrangements, that is, the sensor device may comprise n×m sensor elements that provide data on pressure distribution on n×m areas ($n^2$ if n=m) of the sensor device. This data may be collected, for each sensor element, in the form of an electrical or electronic signal by converting the measurement of the change in resistance (or capacitance or inductance) provided by each sensor element into voltage or intensity and may be provided to the monitoring system 12.

On the other hand, both the sensor device 11 and the monitoring system 12 may comprise a communications module (not shown) to establish a communication between them. If the sensor device and the monitoring system are close enough, they may be wired (for example, through Ethernet technology) or may be connected through wireless short-range communication technologies, for example, Bluetooth (e.g. BLE—Bluetooth Low Energy), NFC, Zigbee or Wi-Fi technology. If the sensor device and the monitoring system are far away, they may be connected through wireless long-range communication technologies such as GSM, GPRS, 3G, 4G, 5G or satellite technology or wired (for example, through optical fiber, ADSL, etc.).

With respect to the monitoring system 12, it may comprise or may be implemented by electronic means, computing means or a combination of them, that is, said electronic or computing means may be used interchangeably so that a part of the described means may be electronic means and the other part may be computing means, or all described means may be electronic means or all described means may be computing means.

Examples of a monitoring system 12 comprising only electronic means (that is, a purely electronic configuration) may be a programmable electronic device such as a CPLD (Complex Programmable Logic Device), an FPGA (Field Programmable Gate Array) or an ASIC (Application-Specific Integrated Circuit).

Examples of a monitoring system 12 comprising only computing means may be a computer system, which may comprise a memory and a processor, the memory being adapted to store a set of computer program instructions, and the processor being adapted to execute these instructions stored in the memory in order to generate the various events and actions for which the monitoring system has been programmed.

The memory may be contained in the processor (e.g. an EEPROM) or may be external. In the case of an external memory, it can be, for example, data storage means such as magnetic disks (e.g., hard disks), optical disks (e.g., DVD or CD), memory cards, flash memory (e.g., pendrives) or solid-state drives (SSD based on RAM, based on flash, etc.). On the other hand, these storage means can be part of the monitoring system 12 itself and/or can be arranged remotely thereto, wired or wirelessly connected. In the case of being remotely arranged, the communication established between the monitoring system and the storage means can be ensured by, for example, username/password, cryptographic keys and/or by an SSL tunnel established in the communication between them.

Therefore, the set of computer program instructions executable by the processor (such as a computer program) may be stored in a physical storage means, such as those mentioned, but may also be carried by a carrier wave (the carrier medium). It can be any entity or device capable of carrying the program, such as electrical or optical, which can be transmitted via electrical or optical cable or by radio or other means. In this way, when the computer program is contained in a signal that can be transmitted directly by means of a cable or other device or means, the carrier means can be constituted by said cable or another device or means.

The computer program may be in the form of source code, object code, a code intermediate source and object code such as in partially compiled form, or in any other form suitable for use in the implementation of the method. The carrier may be any entity or device capable of carrying the computer program.

Alternatively, the carrier may be an integrated circuit in which the computer program is embedded, the integrated circuit being adapted for performing, or for use in the performance of, the relevant methods.

Consequently, the monitoring system 12 may be based on a low-power hardware device like a microcontroller, a SoC, a PSoC (Programmable SoC) or an ASIC, although, in some scenarios, it may be possible to use other hardware like an FPGA, a CPLD (Complex Programmable Logic Device) or a DSP (Digital Signal Processor). The monitoring system can also contain different types of embedded memories to store data and program instructions. In addition, the monitoring system may include other electronic components like oscillators or programming interfaces (e.g., JTAG, ICSP). This way, the monitoring system 12 may also be implemented by using different types of electronic devices. Examples of such devices are Central Processing Units (CPUs), microcontrollers, Field-Programmable Gate Arrays (FPGAs), Application-Specific Integrated Circuits (ASIC) or System-On-Chips (SOCs). CPUs are powerful. Microcontrollers are usually used because they can be reprogrammed easily and they are powerful enough for carrying out the tasks to be performed. FPGAs can be really powerful for performing certain deterministic demanding tasks, but development is not as easy as with microcontrollers. ASICs are designed explicitly for specific applications and thus they are extremely powerful. However, the cost of developing an ASIC is really high (millions of U.S. dollars) and it only compensates when a really high amount of devices is going to be produced. Regarding SoCs, they integrate in a single integrated circuit a powerful microcontroller and several peripherals (e.g., wireless transceivers).

In addition, the monitoring system 12 may also have a hybrid configuration between computing and electronic means. In this case, the system may comprise a memory and a processor to implement computationally part of its functionalities and certain electronic circuits to implement the remaining functionalities.

On the other hand, the monitoring system 12 may comprise several modules, each of which may perform a part of the events and actions for which the control module as a whole has been programmed. If the modules are close enough, they may be wired (for example, through Ethernet technology) or may be connected through wireless short-range communication technologies. If the modules are far away, they may be connected through long-range wireless communication technologies or long-range wired communication technologies. The cited technologies have been previously disclosed.

Following, a description of the monitoring system 12 will be performed based on a configuration in modules. In any case, the monitoring system may have any of the configurations disclosed above.

The monitoring system 12 may comprise the following modules:
- a module (not shown) for receiving signals coming from the sensor device;
- a module 13 for pre-processing the signals received from the sensor device;
- a module 14 for extracting the main features of the pre-processed signals to be used as predictor variables;
- a module 15 for assessing the functional performance of an individual based on the predictor variables.

The key elements of the monitoring system 12 are the signal pre-processing module 13 and the extracting module 14. These modules pre-condition the signals received from the sensor device 11 and extract the main features that will be used as predictors. They are very important since the electrical signals produced by the sensor device are noisy, carry a big quantity of data with a variable number of items. The number of items is variable since the sampling time is not fixed, i.e. it depends on the starting and end time point of collection triggered by the user. Thus, to build the predictor, a method executed by the monitoring system 12 that produces equi-dimensional measurements, selects the most informative features of the measurements in both the time and spectral domain, and more importantly, builds a collection of features describing quantitatively the behaviour of the signals is designed.

In addition, the monitoring system 12 may further comprise a module 16 for detecting whether any of the received signals coming from the sensor device 11 is wrong.

The signal pre-processing module 13 works as a signal pre-conditioning interface of all the signals collected from the sensor device 11 to be digested by the rest of the modules of the monitoring system 12. This way, the objective of this module is to adapt the signals coming from the firmware of the sensor device and prepare them to be processed by the downstream modules.

Inputs of the pre-processing module 13 are the signals coming from the sensor device 11 in the form of a tridimensional tensor $N_r \times N_c \times N_S$ of the measurement of a matrix at each time instant, where $N_r$ and $N_c$ are the number of rows and columns, respectively, of the array sensor, and $N_S$ is the number of time instants. The output of the pre-processing module 13 is a vector V with the preprocessed signals across all the sampling period.

More specifically, for each sampling time, the sensor device 11 produces an $N_r \times N_c$ measurement matrix, where $N_r$ and $N_c$ are the number of rows and columns of the array sensor. In some examples, $N_r = N_c = 16$, however this number can be changed in the range of, for example, [8 32].

For each replicate r of each individual, the sensor device 11 produces a three-dimensional tensor $T_S$ of order $N_r \times N_c \times N_S$. In some examples, $N_S$ may be in the range of, for example, [100 280]. The final sampling time of each replicate depends on the response time of the supervisor.

To produce equi-order tensors with all the $3^{rd}$ dimension on the same length $N_{MAX}$, the initial tensor $T_S$ will be reformatted using the following rules:

If $N_S \geq N_{MAX}$ the $3^{rd}$ dimension of the tensor $T_S$ is truncated to the length $N_{MAX}$. Therefore, the tensor $T_S$ is transformed into a tensor $T_{MAX}$ of dimensions $N_r \times N_c \times N_{MAX}$.

If $N_S \geq N_{MAX}$ the $3^{rd}$ dimension of the tensor $T_S$ is padded to the length $N_{MAX}$. The padding strategy is based on attaching after the $N_r \times N_c \times N_S$ tensor a padding tensor $T_p$ of dimensions $N_r \times N_c \times N_p$, where $N_p$ is the padding length $N_p = N_{max} - N_S$ that is attached after the tensor $T_S$, thus creating a tensor $T_{MAX}$ of dimensions $N_r \times N_c \times N_{MAX}$:

$$T_{Max} = (T_S | T_p)$$

The padding value $v_p$ is chosen to be the maximum of all the $N_r \times N_c \times N_S$ values of the tensor $T_S$:

$$v_p = \max_{1 \leq k \leq N_S, 1 \leq j \leq N_c, 1 \leq i \leq N_r} T_S(k, j, i)$$

This value is used to pad uniformly the $N_r \times N_c \times N_p$ elements of the padding tensor $T_p$. To filter glitches other strategies different from the maximum can be used to chosen to select the padding value $v_p$.

If $N_S=N_{MAX}$ just rename $T_S$ as $T_{MAX}$.

Thus, in any of the aforementioned three case it is possible to finish always with a tensor $T_{MAX}$ of dimensions $N_r \times N_c \times N_{MAX}$. The number $N_{MAX}$ may be chosen to be, for example, in the range of [180 280].

Next, the $N_r \times N_c \times N_{MAX}$ tensor $T_{MAX}$ is vectorized into an $N_{MAX}$ length vector V, in which to each position i in [1 $N_{MAX}$] is assigned the sum of the elements of the $N_r \times N_c$ matrix in the position i of the $T_{MAX}$ tensor. Thus, $$V(i) = \sum_{j=1}^{N_r} \sum_{k=1}^{N_c} T_{MAX}(k, j, i), \ 1 \le i \le N_{MAX}$$

The sensor device 11 produces a resting background signal when not pressure is applied on it. Such background signal is not always the same in each case. Therefore, to avoid this effect, a background correction of the vector V is implemented. The background correction is implanted by subtracting from each element of V the value of the minimum element of V, $V_{MIN}$.

$$V_{MIN} = \min_{1 \le i \le N_{MAX}} V(i)$$

Thus, the background corrected signal $V_b$ is:

$$V_b(i) = V(i) - V_{MIN}, 1 \le i \le N_{MAX}$$

Figure 9:
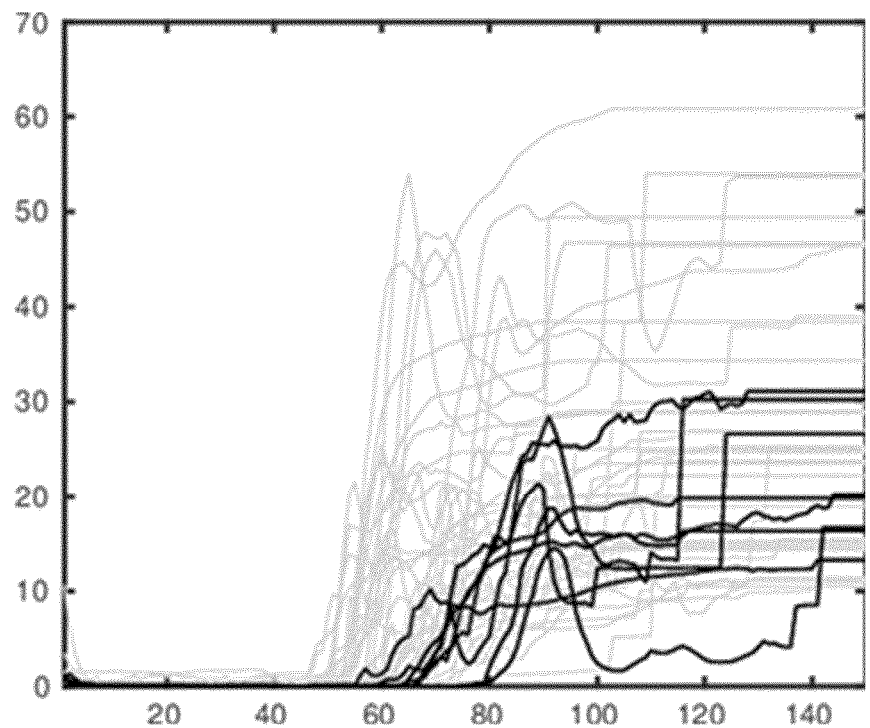
FIG. 9 shows a graph representing time profiles after vectorization and background correction.

Several time profiles $V_b$ after vectorization and background correction are depicted in FIG. 9.

If $N_r$ replicates of vectorized measurements $V^r$, $1 \le i \le N_r$ have been carried out for an individual (for example, a patient) in the same session, and $V_b^r$ are their corresponding background corrected signals, then it is possible to choose as the representative vectorized background corrected signal $V_b$ the average of all the replicates in its sampling time i, and the system produces a unique vector $V_b$ for each patient using the following equation:

$$V_b(i) = \frac{\sum_{r=1}^{N_r} v_b^r(i)}{N_r}, \ 1 \le i \le N_{MAX},$$

where $N_r$ is the number or replicates that have been performed over the same individual in the same session. $N_r$ may be, for example, in the range of [1 5].

The objective of the extracting module 14 is to summarize the vector $V_b$ signal (obtained previously by the pre-processing module 13) in a compact way to be more easily processed by the downstream modules. The vector $V_b$ has a variable length, and its signal behaves in a noise complicated way. These two features make this vector difficult for manipulation by the downstream modules. The transformation of this vector to a collection of descriptive variables with fixed dimensions and robust to the noise solves the aforementioned drawbacks.

The input of this extracting module 14 is the vector $V_b$ with the pre-processed signals across all the sampling periods from the signal processing module and the output is a collection of predictor variables $V^P = (V^{DESCRIPTIVE} | V^{TIME} | V^{FREQUENCY})$ that summarize the behavior of the vector $V_b$ of the pre-processed signals.

More specifically, the predictor variables may be selected from three categories:

Category I: Signal descriptive variables in the time domain: $V^{DESCRIPTIVE}$

Figure 10:
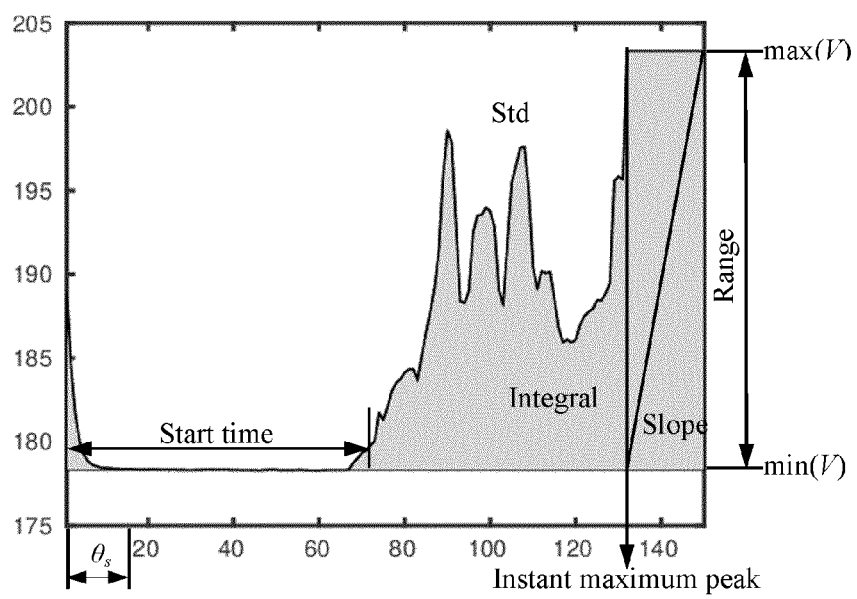
FIG. 10 shows a graph in which the main parameters and the auxiliary parameters used for defining the descriptive variables over a time profile are indicated.

It may belong to this category the following variables (see FIG. 10):

Range of variation of the signal: $R = \max(V_b) - \min(V_b)$;

Instant of the maximum peak $I_{Max} = (\text{index max}(V_b))$;

Standard deviation of the signal Std, normalizing by the length−1 of the vector $V_b$, to produce the second moment of the sample about its mean;

Slope S of the signal defined as the ratio between the Range and the instant of the maximum peak;

Start time of change of the signal Sta. The start time is taken after passing a threshold $\theta_s$ of a period of stabilization of the electrical signal taken by the sensor in the range of, for example, [3 20], with the condition that after such period the signal has to change at least in the range of, for example, [3 10];

Integral ∫ of the signal calculated as the sum of all its values in the interval of, for example, [1 $N_{Max}$]. The integral of the signal is calculated as follows:

$$\text{Integral} = \sum_{i=1}^{N_{MAX}} V_b(i)$$

Thus, $V^{DESCRIPTIVE} = (R, I_{max}, \text{Std}, S, \text{Sta}, \int)$.

Figure 11:
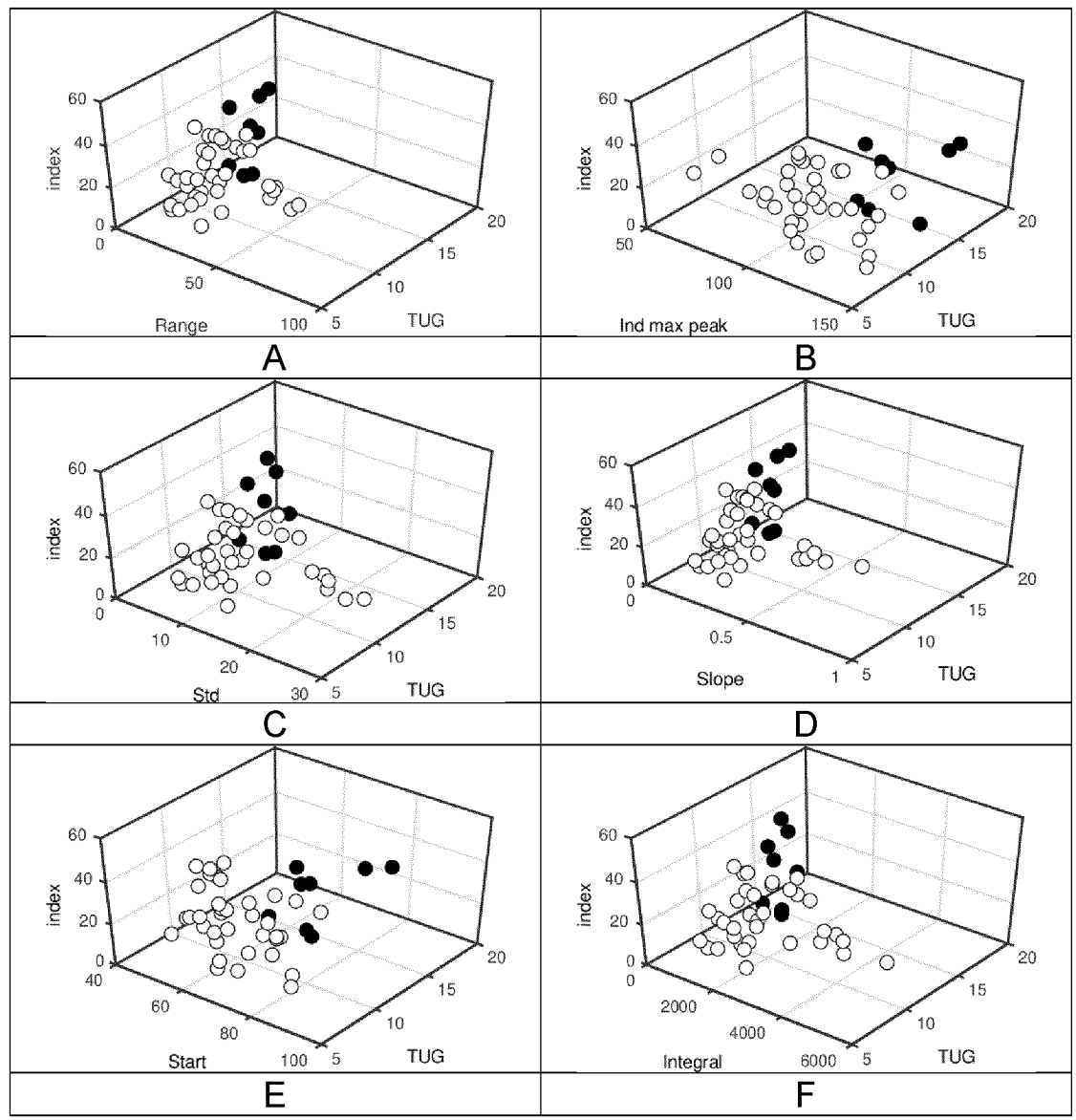
FIG. 11 shows three-dimensional scatter plots of signal descriptive variables.

A three-dimensional scatter plot of the signal descriptive variables is given in FIG. 11. In said figure are represented the following variables: (A) Range, (B) Time index of the maximum peak, (Std) standard deviation, (D) Slope, (E) Start time of change of the signal, (F) Integral of the signal. All of them are depicted together with the anonymized index of the individual and the TUG (it will be disclosed later). It is possible to use an anonymized index of the individual not because it is a descriptive variable but to reduce the point overlapping effect. The Robust and Fragile cases are depicted with white and black circles (it will be disclosed later).

Category II: Signal time series variables in the time domain: $V^{TIME}$

It may belong to this category the variables expressed in the time domain. To obtain them it is possible to perform the following steps:

filtering the noise of the vector $V_b$, $V_b$ being filtered with a smoothing moving window. The length $W_S$ of the smoothing window may be in the range of, for example, [2 50];

reducing the sample length of the resulting $V_b$ vector by decimation factor of d in the range of, for example, [2 50], so that the length of the resulting decimate vector is $\lceil (\text{length}(V_b))/d \rceil$ where $\lceil \ \rceil$ is the ceil operator. To obtain this reduced length, vector $V_b$ may be decimated using one of several possible alternatives:

A simple resampling of $V_b$ each time d.

Using a lowpass Chebyshev Type I Infinite Impulse Response (IIR) filter of order in the range of, for example, [4, 12].

Using a Finite Impulse Response (FIR) filter with and order in the range of, for example, [10 50] with a Hamming window.

The final signal time series variables $V^{TIME}$ are the $\lceil (\text{length}(V_b))/d \rceil$ elements of the $V_b$ decimated vector: $V_b^d$.

Category III: Signal Spectral Variables in the Frequency Domain, $V^{FREQUENCY}$ It may belong to this category variables expressed in the frequency domain. To obtain them the spectral power of the vector $V_b$ is calculated as follows:
1. The vector length is truncated to the floor $L_T$ of maximum power of 2 of the length of the vector $V_b$;
2. The fast Fourier transform FFT is applied to the truncated signals using a Discrete Fast Fourier (DFT) method:

$$FFT(k) = \sum_{j=1}^{L_T} V_b(j) W_{L_T}^{(j-1)(k-1)}$$

where $W_{L_T} = e^{(2\pi i)L_T}$
3. The spectral power P is calculated:

$P(k) = |FFT(k)|/N_L$

4. The spectral power vector is truncated to a length in the range of, for example, [2 32], thus producing the final signal spectral variables in the frequency domain: $V^{FREQUENCY}$.

Next, based on the three types of predictor variables (I) Signal descriptive variables $V^{DESCRIPTIVE}$ (II) Signal time series variables $V^{TIME}$ and (III) Signal spectral variables $V^{FREQUENCY}$, it is possible to calculate their respective maximum ($V_{Max}^{DESCRIPTIVE}|V_{max}^{TIME}|V_{Max}^{FREQUENCY}$) and minimum $V_{Min}^{DESCRIPTIVE}|V_{Min}^{TIME}|V_{Min}^{FREQUENCY}$) values and use them to normalize the data between 0 and 1.

Finally, all the normalised variables of each of the three categories are attached in a vector to build the vector of predictive variables of each individual:

$V^P = (V^{DESCRIPTIVE}|V^{TIME}|V^{FREQUENCY})$

After attaching all the predictor variables, the resulting matrix is normalized between 0 and 1.

When the module 15 for assessing the functional performance of an individual comprises a module for identifying the state of fragility or robustness of the individual, the objective of the module is to classify or identify whether an individual is fragile or robust. The input of this module is the collection of predictor variables $V^P = (V^{DESCRIPTIVE}|V^{TIME}|V^{FREQUENCY})$ that summarize the behavior of the vector $V_b$ of the pre-processed signals and for each individual used to train the system bimodal class value C marking whether the individual is fragile (C=1) or whether is robust (C=1). The output of the module is a bimodal class value C marking whether the individual is fragile or robust, and a value that gives the probability of the assignment.

More specifically, to predict or identify the state of fragility or robustness of the individual, an Artificial Neural Network (ANN) with the following topology may be used:
- An input layer with as many neurons as predictor variables chosen;
- at least one hidden layer with a number or neurons in the range of, for example, [2 10];
- at least one output layer with at least one neuron.

As transfer functions defining to calculate the output of each neuron of each layer it is possible to use the Competitive transfer function, Elliot sigmoid transfer function, Positive hard limit transfer function, Symmetric hard limit transfer function, Logarithmic sigmoid transfer function, Inverse transfer function, Positive linear transfer function, Linear transfer function, Radial basis transfer function, Radial basis normalized transfer function, Positive saturating linear transfer function, Symmetric saturating linear transfer function, Soft max transfer function, Symmetric sigmoid transfer function and Triangular basis transfer function among others.

As learning method, it is possible to use the stochastic gradient descent with momentum (SDGM), backpropagation methods such as the Broyden-Fletcher-Goldfarb-Shanno (BFGS) quasi-Newton backpropagation, conjugate gradient backpropagation with Powell-Beale, Fletcher-Reeves, or Polak-Ribiere restarts, the gradient descent backpropagation, the gradient descent with adaptive lr backpropagation, the gradient descent with momentum, the gradient descent w/momentum & adaptive lr backpropagation, the one step secant backpropagation, the resilient backpropagation (RPROP), the scaled conjugate gradient backpropagation.

During the training phase of the ANN, the input layer is feed with the collection of predictor variables $V^p$ of the training individuals and the output layer with the bimodal class value C of the training individuals. During the test phase, the input layer is feed with the collection of predictor variables $V^P$ of the test individuals and the output layer with the bimodal class value C of the test individuals.

The result of the training of the Artificial Neural Network is shown in the confusion matrix of FIG. 13. In said figure, Confusion matrix. The rows correspond to the predicted class (predicted TUG) and the columns to the measure class (measured TUG). The diagonal cells show for how many (top number), and in what percentage (bottom number) of the examples the trained network estimates correctly the classes of observations, that is, it shows what percentage of the true and predicted classes match. The off-diagonal cells show where the classifier has made mistakes, the cells in this case show for how many (top number), and in what percentage (bottom number) of the examples the trained network wrongly the classes of observations. The column on the far right of the table shows the accuracy for each predicted class (on top the percentage of corrected predicted in each category and on bottom the percentage of predictions that are wrong). The row at the bottom of the plot shows the accuracy for each true class (on top in green the percentage of corrected predicted in each category and on bottom in red the percentage of predictions that are wrong). The cell in the bottom right of the plot shows the overall accuracy (on top the percentage of predictions that are correct and on bottom the percentage of predictions that are wrong).

When the module 15 for assessing the functional performance of an individual comprises a module for predicting the value of the TUG (Timed Up Go) test of an individual, the objective is to predict in seconds the value of the TUG (Timed Up GO) test. The TUG predictor modules use as independent variables the chosen predictor variables. The input of the module is the collection of predictor variables $V^P = (V^{DESCRIPTIVE}|V^{TIME}|V^{FREQUENCY})$ that summarize the behavior of the vector $V_b$ of the pre-processed signals and the measured value of the TUG (Timed Up GO) test of each individual used to train the system. The output of the module is the measured TUG scaled between 0 and 1. The independent variables are used together with a unit vector of the same length as the number individuals to fit a linear regression model of the scaled TUG target.

As regressor method, a multiple linear regression with the least square optimization may be used. However other methods can also be applied such as a robust fit using a weight function w( ) among others:
- Andrews function $w = (abs(k) < \pi) \sin(k)/k$
- Bisquare function $w = (abs(k) < 1)(1-k^2)^2$ Cauchy function w=1/(1+k²)
Fair function w=1/(1+abs(k))
Huber function w=1/max(1, abs(k))
Logistic function w=tan h(k)/k
Talwar function w=(abs(k)<1)
Welsch function w=exp(−(k²))
where k is a parameter. It is possible to use non-linear regressors such as quadratic polynomial piecewise linear interpolation smoothing splines and local linear regression, lowess, among others.

After obtained the regression parameters b using one of the aforementioned regression methods the $TUG^{Reg}$ values are obtained by the expression:

$$TUG^{Reg} = b \times V_p$$

To obtain the final prediction of TUG, $TUG^{Pred}$, the output of the regression model $TUG^{Reg}$ is rescaled using the expression:

$$TUG^{Pred} = TUG^{Reg} \times (TUG^{Max} - TUG^{Min}) + TUG^{Min}$$

where $TUG^{Max}$ and $TUG^{Min}$ are the maximum and the minimum of the measured TUG of all the individuals.

Figure 12:
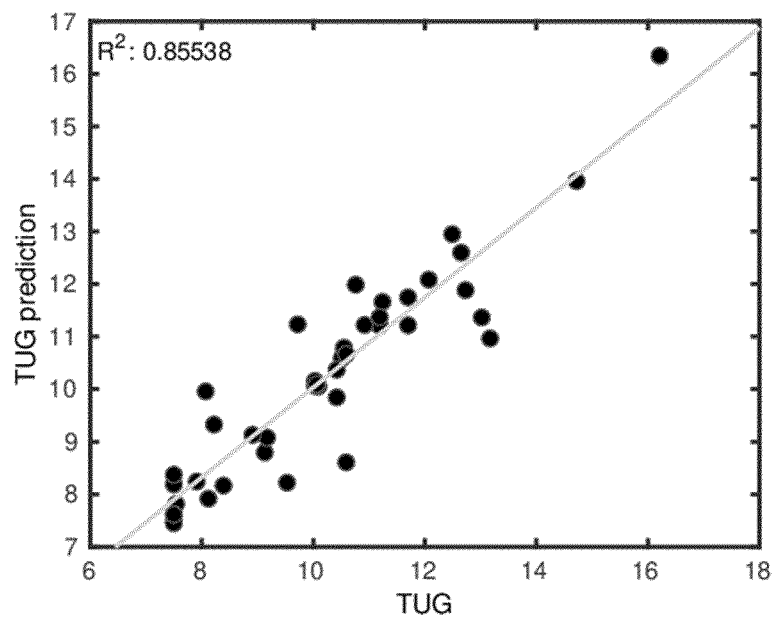
FIG. 12 shows a graph representing a regression of a predicted $TUG^{Pred}$ versus the measured TUG.

An example of the predicted TUG values versus the real ones is depicted in FIG. 12.

In some examples, the module 15 for assessing the functional performance of an individual may comprise a module for identifying individuals with high risk of fractures and other health related adverse outcomes. Said identification may be based on the results of the TUG test previously disclosed because there is a correlation with them. The TUG test has demonstrated the ability to identify this type of individuals.

The objective of the module 16 for detecting whether any of the received signals coming from the sensor device 11 is wrong, is to detect whether the sensor device is producing wrong measurements. These wrong measurements can be due to wrong manipulations by the person using the sensor or by hardware failures. The input of the module is the vector $V_b$ provided by the pre-processing module 13 with the pre-processed signals across all the sampling period from the signal processing module. The output may be a warning signal that triggers a visual, haptic and/or a sound alarm.

This module 16 is convenient for troubleshooting. If the person using the sensor proceeds correctly following the instructions and there are no hardware problems, this module will not generate signals. However, in the event of any manipulation error or hardware damage, the module generates a signal that will help avoid downstream problems.

In some cases, due to the fact that the sensor device 11 is operated by several users, and due to the different conditions taking measurements of potentially impaired individuals, it is possible that the collected signal is not valid, and that wrong collection could pass unnoticed by the human supervisor. There are two main reasons that a collection of measurement could be wrong:
  a) The sensor device did not collect all the samples during a sufficiently long period of time $N_S$, due to sensor error or to a mistake of the operator pressing the button to end prematurely the collection of data.
  b) Bad adjustment of the sensor device to the seat or the like, or a bad adjustment of the plugging systems, so that the sensor device does not allow recording the entire amplitude of the electrical signals.

To reject such cases, said module 16 detects the wrong signals if one or the two following conditions happens has been implemented:

a) The length of the recorded sample is shorter than $N_S$.
  b) The maximum of the signal across the recording period is less than a threshold $\theta_{Max}$ in the range of, for example, [3 10].

The individual records whose signals do not fulfil the aforementioned conditions are rejected by the module 16. In addition, triggering a warning to the user is allowed. A warning may be generated, for example, by at least one of the following actuator elements:
  at least one actuator element configured to generate an audible signal (e.g. a speaker, a buzzer, etc.);
  at least one actuator element configured to generate a visual signal (e.g. a display screen (for example, LCD), a plurality of LEDs (Light Emitting Diode), etc.);
  at least one actuator element configured to generate a haptic signal (e.g. a vibrator motor).

Figure 14:
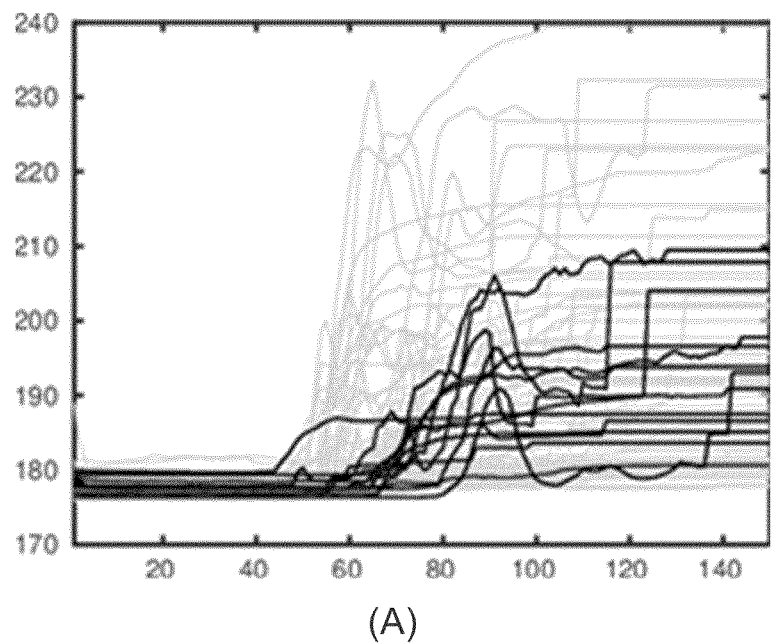
FIG. 14 shows a first graph (A) representing time profiles after vectorization before removal of wrong records and a second graph (B) representing time profiles after vectorization after removal of wrong records.
Figure 14:
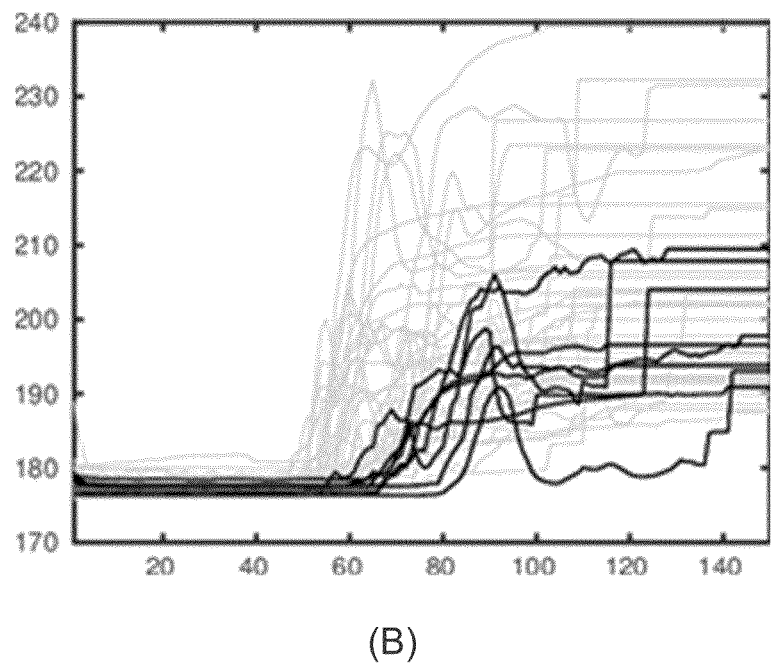

FIG. 14 shows a first graph (A) representing time profiles after vectorization and before removal of wrong records and a second graph (B) representing time profiles after vectorization and after removal of wrong records, that is, time profiles after passing through the module 16 for detecting whether any of the received signals coming from the sensor device 11 is wrong. It is important to note that the robust and fragile cases are depicted in the graphs (A) and (B) in grey and black lines, respectively.

In any case, the monitoring system 12 may be configured to execute a method of assessing the functional performance of an individual as described above. This way, the method may comprise:
  receiving signals coming from the sensor device 11;
  pre-processing the signals received from the sensor device;
  extracting the main features of the pre-processed signals to be used as predictor variables;
  assessing the functional performance of an individual based on the predictor variables.

In addition, the method may comprise detect whether any of the received signals coming from the sensor device is wrong.

When the sensor device 11 comprises an array of sensors of $N_r \times N_c$ that produces a $N_r \times N_c$ measurement matrix for each sampling time and the received signals are in the form of a tri-dimensional tensor $T_S$ of order $N_r \times N_c \times N_S$, where $N_r$ is the number of rows of the array of sensors, $N_c$ is the number of columns of the array of sensors, and $N_S$ is the number of sampling times, step of pre-processing the signals received from the sensor device may comprise:
  producing an equi-order tensor $T_{MAX}$ of dimensions $N_r \times N_c \times N_{MAX}$;
  vectoring the produced equi-order tensor $T_{MAX}$ into a vector V of length $N_{MAX}$, in which to each position i in [1 $N_{MAX}$] is assigned the sum of the elements of the $N_r \times N_c$ measurement matrix in the position i of the tensor $T_{MAX}$.

Producing an equi-order tensor $T_{MAX}$ of dimensions $N_r \times N_c \times N_{MAX}$ may comprise:
  reformatting the tri-dimensional tensor $T_S$ of order $N_r \times N_c \times N_S$ according to:
    if $N_S \geq N_{MAX}$, truncating the third dimension of the tensor $T_S$ to the length $N_{MAX}$, transforming the tensor $T_S$ into a tensor $T_{MAX}$ of dimensions $N_r \times N_c \times N_{MAX}$;
    if $N_S \leq N_{MAX}$, padding the third dimension of the tensor $T_S$ to the length $N_{MAX}$, transforming the tensor $T_S$ into a tensor $T_{MAX}$ of dimensions $N_r \times N_c \times N_{MAX}$;
    if $N_S = N_{MAX}$, renaming $T_S$ as $T_{MAX}$.

Padding the third dimension of the tensor $T_S$ to the length $N_{MAX}$, if $N_S \leq N_{MAX}$, may comprise attaching after the tensor $T_S$ of order $N_r \times N_c \times N_S$ a padding tensor $T_p$ of dimensions $N_r \times N_c \times N_p$, where $N_p$ is the padding length $N_p = N_{MAX} - N_S$.

Pre-processing the signals received from the sensor device may further comprise correcting the background of the vector V for obtaining a background corrected vector $V_b$. Correcting the background of the vector V may comprise subtracting from each element of vector V the value of the minimum element of V, $V_{MIN}$, such that a background corrected vector $V_b$ is obtained.

Extracting the main features of the pre-processed signals to be used as predictor variables, predictor variables being signal descriptive variables in the time domain, may comprise obtaining the signal descriptive variables in the time domain vector $V^{DESCRIPTIVE}$.

Extracting the main features of the pre-processed signals to be used as predictor variables, predictor variables being signal time series variables in the time domain, may comprise:
- filtering the noise of the background corrected vector $V_b$ with a smoothing moving window;
- reducing the sample length of the filtered vector $V_b$ by decimation factor of d, such that the signal time series variables in the time domain vector $V^{TIME}$ is obtained.

Reducing the sample length of the filtered vector $V_b$ by decimation factor of d may comprise at least the following:
- applying a simple resampling of $V_b$ each time d;
- applying a lowpass Chebyshev Type I Infinite Impulse Response (IIR) filter;
- applying a Finite Impulse Response (FIR) filter with a Hamming window.

Extracting the main features of the pre-processed signals to be used as predictor variables, predictor variables being signal spectral variables in the frequency domain, may comprise:
- truncating the background corrected vector $V_b$ length to the floor operator $L_T$ of maximum power of 2 of the length of the vector $V_b$;
- applying a Fast Fourier transform to the truncated vector $V_b$ using a Discrete Fast Fourier method;
- obtaining the spectral power P of the vector $V_b$ based on the result of applying the Fast Fourier transform to the truncated vector $V_b$;
- truncating the obtained spectral power vector, such that the signal spectral variables in the frequency domain vector $V^{FREQUENCY}$ is obtained.

Extracting, the main features of the pre-processed signals to be used as predictor variables may further comprise:
- obtaining the respective maximum and minimum values of the obtained predictor variables $V^{DESCRIPTIVE}$, $V^{TIME}$ and/or $V^{FREQUENCY}$.
- normalizing, based on the obtained maximum and minimum values, between 0 and 1, the obtained predictor variables;
- attaching in a vector $V_P$ the normalized predictor variables $V^{DESCRIPTIVE}$, $V^{TIME}$ and/or $V^{FREQUENCY}$.

Detecting whether any of the received signals coming from each sensor of the array of sensors is wrong may comprise:
- rejecting a received signal if at least one of the following conditions are fulfilled:
  - the length of the recorded sample is shorter than $N_S$;
  - the maximum of the signal across the recording period is less than a predetermined threshold $\theta_{MAX}$.

Detecting whether any of the received signals coming from each sensor of the array of sensors is wrong may further comprise, if a received signal is rejected, generating a warning about the rejection of the signal.

Assessing the functional performance of an individual based on the extracted predictor variables may comprise:
- predicting the value of the TUG (Timed Up Go) test of the individual based on the extracted predictor variables $V^P$;
- assessing the functional performance of an individual based on the predicted value of the TUG test.

Predicting the value of the TUG (Timed Up Go) test of the individual based on the extracted predictor variables may comprise:
- applying a regression method taking into account the extracted predictor variables $V^P$;
- rescaling the output of the regression method to obtain the final prediction of TUG.

Assessing the functional performance of an individual based on the extracted predictor variables may comprise identifying the state of fragility or robustness of the individual based on the extracted predictor variables $V^P$. Identifying the state of fragility or robustness of the individual based on the extracted predictor variables may comprise using an Artificial Neural Network to predict the state of fragility or robustness of the individual, the Artificial Neural Network having a topology of at least one input layer comprising as many neurons as predictor variables are obtained, at least one hidden layer with a predetermined number of neurons, at least one output layer with at least one neuron.

Assessing the functional performance of an individual based on the extracted predictor variables may comprise identifying individuals with high risk of fractures and other health related adverse outcomes based on the extracted predictor variables.

Identifying individuals with high risk of fractures and other health related adverse outcomes based on the extracted predictor variables may comprise:
- predicting the value of the TUG (Timed Up Go) test of the individual based on the extracted predictor variables $V^P$;
- identifying individuals with high risk of fractures and other health related adverse outcomes based on the predicted value of the TUG test.

This way, the monitoring system 12 may be configured to execute the described method of assessing the functional performance of an individual.

On the other hand, the monitoring system 12 may comprise a memory and a processor, embodying instructions stored in the memory and executable by the processor, the instructions comprising functionality to execute the described method of assessing the functional performance of an individual.

The invention also relates to a non-transitory computer program product that causes a managing system 12 to perform a method of assessing the functional performance of an individual.

In addition, the invention relates to a computer-readable medium having thereon computer-executable instructions, the computer-executable instructions upon execution configuring a monitoring system 12 to perform a method of assessing the functional performance of an individual.

For reasons of completeness, various aspects of the present disclosure are set out in the following numbered clauses:

Clause 1. A system for assessing the functional performance of an individual, the system comprising:
- a sensor device;
- a monitoring system, connectable to the sensor device, configured to:

receive signals coming from the sensor device;
pre-process the signals received from the sensor device;
extract the main features of the pre-processed signals to be used as predictor variables;
assess the functional performance of an individual based on the predictor variables.

Clause 2. The system according to clause 1, the monitoring system being configured to:
detect whether any of the received signals coming from the sensor device is wrong.

Clause 3. The system according to any of clauses 1 or 2, wherein the sensor device comprises an array of sensors of $N_r \times N_c$ that produces a $N_r \times N_c$ measurement matrix for each sampling time; wherein received signals are in the form of a tri-dimensional tensor $T_S$ of order $N_r \times N_c \times N_S$, where $N_r$ is the number of rows of the array of sensors, $N_c$ is the number of columns of the array of sensors, and $N_S$ is the number of sampling times; wherein pre-processing, by the monitoring system, the signals received from the sensor device comprises:
producing an equi-order tensor $T_{MAX}$ of dimensions $N_r \times N_c \times N_{MAX}$;
vectoring the produced equi-order tensor $T_{MAX}$ into a vector V of length $N_{MAX}$, in which to each position i in [1 $N_{MAX}$] is assigned the sum of the elements of the $N_r \times N_c$ measurement matrix in the position i of the tensor $T_{MAX}$.

Clause 4. The system according to clause 3, wherein producing, by the monitoring system, an equi-order tensor $T_{MAX}$ of dimensions $N_r \times N_e \times N_{MAX}$ comprises:
reformatting the tri-dimensional tensor $T_S$ of order $N_r \times N_c \times N_S$ according to:
if $N_S \geq N_{MAX}$, truncating the third dimension of the tensor $T_S$ to the length $N_{MAX}$, transforming the tensor $T_S$ into a tensor $T_{MAX}$ of dimensions $N_r \times N_c \times N_{MAX}$
if $N_S \leq N_{MAX}$, padding the third dimension of the tensor $T_S$ to the length $N_{MAX}$, transforming the tensor $T_S$ into a tensor $T_{MAX}$ of dimensions $N_r \times N_c \times N_{MAX}$
if $N_S = N_{MAX}$, renaming $T_S$ as $T_{MAX}$.

Clause 5. The system according to clause 4, wherein padding, by the monitoring system, the third dimension of the tensor $T_S$ to the length $N_{MAX}$, if $N_S \leq N_{MAX}$, comprises:
attaching after the tensor $T_S$ of order $N_r \times N_c \times N_S$ a padding tensor $T_p$ of dimensions $N_r \times N_c \times N_P$, where $N_p$ is the padding length $N_p = N_{MAX} - N_S$.

Clause 6. The system according to any of clauses 1 to 5, wherein pre-processing, by the monitoring system, the signals received from the sensor device comprises:
correcting the background of the vector V for obtaining a background corrected vector $V_b$.

Clause 7. The system according to clause 6, wherein correcting, by the monitoring system, the background of the vector V comprises:
subtracting from each element of vector V the value of the minimum element of V, $V_{MIN}$, such that a background corrected vector $V_b$ is obtained.

Clause 8. The system according to any of clauses 1 to 7, wherein extracting, by the monitoring system, the main features of the pre-processed signals to be used as predictor variables, predictor variables being signal descriptive variables in the time domain, comprises:
obtaining the signal descriptive variables in the time domain vector $V^{DESCRIPTIVE}$.

Clause 9. The system according to clause 8, wherein signal descriptive variables in the time domain are selected from at least one of the following:
Range of variation of the signal;
Instant of the maximum peak of the signal;
Standard deviation of the signal;
Slope of the signal defined as the ratio between the range and the instant of the maximum peak;
Start time of change of the signal;
Integral of the signal.

Clause 10. The system according to any of clauses 7 to 9, wherein extracting, by the monitoring system, the main features of the pre-processed signals to be used as predictor variables, predictor variables being signal time series variables in the time domain, comprises:
filtering the noise of the background corrected vector $V_b$ with a smoothing moving window;
reducing the sample length of the filtered vector $V_b$ by decimation factor of d, such that the signal time series variables in the time domain vector $V^{TIME}$ is obtained.

Clause 11. The system according to clause 10, wherein reducing, by the monitoring system, the sample length of the filtered vector $V_b$ by decimation factor of d comprises at least of the following:
applying a simple resampling of $V_b$ each time d;
applying a lowpass Chebyshev Type 1 Infinite Impulse Response (IIR) filter;
applying a Finite Impulse Response (FIR) filter with a Hamming window.

Clause 12. The system according to any of clauses 7 to 11, wherein extracting, by the monitoring system, the main features of the pre-processed signals to be used as predictor variables, predictor variables being signal spectral variables in the frequency domain, comprises:
truncating the background corrected vector $V_b$ length to the floor operator $L_T$ of maximum power of 2 of the length of the vector $V_b$;
applying a Fast Fourier transform to the truncated vector $V_b$ using a Discrete Fast Fourier method;
obtaining the spectral power P of the vector $V_b$ based on the result of applying the Fast Fourier transform to the truncated vector $V_b$;
truncating the obtained spectral power vector, such that the signal spectral variables in the frequency domain vector $V^{FREQUENCY}$ is obtained.

Clause 13. The system according to any of clauses 8 to 12, wherein extracting, by the monitoring system, the main features of the pre-processed signals to be used as predictor variables comprises:
obtaining the respective maximum and minimum values of the obtained predictor variables $V^{DESCRIPTIVE}$, $V^{TIME}$ and/or $V^{FREQUENCY}$;
normalizing, based on the obtained maximum and minimum values, between 0 and 1, the obtained predictor variables;
attaching in a vector $V^P$ the normalized predictor variables $V^{DESCRIPTIVE}$, $V^{TIME}$ and/or $V^{FREQUENCY}$.

Clause 14. The system according to any of clauses 2 to 13, wherein detecting, by the monitoring system, whether any of the received signals coming from each sensor of the array of sensors is wrong comprises:
rejecting a received signal if at least one of the following conditions are fulfilled:
the length of the recorded sample is shorter than $N_S$;
the maximum of the signal across the recording period is less than a predetermined threshold $\theta_{MAX}$.

Clause 15. The system according to clause 14, wherein detecting, by the monitoring system, whether any of the received signals coming from each sensor of the array of sensors is wrong comprises, if a received signal is rejected:

generating a warning about the rejection of the signal.

Clause 16. The system according to any of clauses 1 to 15, wherein assessing, by the monitoring system, the functional performance of an individual based on the extracted predictor variables comprises:
predicting the value of the TUG (Timed Up Go) test of the individual based on the extracted predictor variables $V^P$;
assessing the functional performance of an individual based on the predicted value of the TUG test.

Clause 17. The system according to clause 16, wherein predicting, by the monitoring system, the value of the TUG (Timed Up Go) test of the individual based on the extracted predictor variables comprises:
applying a regression method taking into account the extracted predictor variables $V^P$;
rescaling the output of the regression method to obtain the final prediction of TUG.

Clause 18. The system according to clause 17, wherein the regression method is selected from at least one of the following:
linear regression method such as a multiple linear regression method with the least square optimization;
a robust fit method using a weight function w( );
a non-linear regression method such as quadratic polynomial piecewise linear interpolation smoothing splines;
local linear regression method.

Clause 19. The system according to clause 18, wherein the robust fit method using a weight function w( ) comprises at least one of the following:
Andrews function w=(abs(k)<π) sin(k)/k
Bisquare function w=(abs(k)<1) (1−k2)2
Cauchy function w=1/(1+k2)
Fair function w=1/(1+abs(k))
Huber function w=1/max(1, abs(k))
Logistic function w=tan h(k)/k
Talwar function w=(abs(k)<1)
Welsch function w=exp(−(k2))
where k is a parameter.

Clause 20. The system according to any of clauses 1 to 15, wherein assessing, by the monitoring system, the functional performance of an individual based on the extracted predictor variables comprises:
identifying the state of fragility or robustness of the individual based on the extracted predictor variables $V^P$.

Clause 21. The system according to clause 20, wherein identifying, by the monitoring system, the state of fragility or robustness of the individual based on the extracted predictor variables comprises:
using an Artificial Neural Network to predict the state of fragility or robustness of the individual, the Artificial Neural Network having a topology of at least one input layer comprising as many neurons as predictor variables are obtained, at least one hidden layer with a predetermined number of neurons, at least one output layer with at least one neuron.

Clause 22. The system according to clause 21, wherein the transfer function to calculate the output of each neuron of each layer is selected from at least one of the following:
Competitive transfer function;
Elliot sigmoid transfer function;
Positive hard limit transfer function;
Symmetric hard limit transfer function;
Logarithmic sigmoid transfer function;
Inverse transfer function;
Positive linear transfer function;
Linear transfer function;
Radial basis transfer function;
Radial basis normalized transfer function;
Positive saturating linear transfer function;
Symmetric saturating linear transfer function;
Soft max transfer function;
Symmetric sigmoid transfer function;
Triangular basis transfer function.

Clause 23. The system according to any of clauses 21 or 22, wherein the learning method is selected from at least one of the following:
Stochastic gradient descent with momentum (SDGM);
Backpropagation methods such as the Broyden-Fletcher-Goldfarb-Shanno (BFGS) quasi-Newton backpropagation, conjugate gradient backpropagation with Powell-Beale, Fletcher-Reeves, or Polak-Ribiere restarts, the gradient descent backpropagation, the gradient descent with adaptive IR backpropagation, the gradient descent with momentum, the gradient descent w/momentum & adaptive IR backpropagation; the one step secant backpropagation, the resilient backpropagation (RPROP), the scaled conjugate gradient backpropagation.

Clause 24. The system according to any of clauses 1 to 15, wherein assessing, by the monitoring system, the functional performance of an individual based on the extracted predictor variables comprises:
identifying individuals with high risk of fractures and other health related adverse outcomes based on the extracted predictor variables.

Clause 25. The system according to clause 24, wherein identifying, by the monitoring system, individuals with high risk of fractures and other health related adverse outcomes based on the extracted predictor variables comprises:
predicting the value of the TUG (Timed Up Go) test of the individual based on the extracted predictor variables $V^P$;
identifying individuals with high risk of fractures and other health related adverse outcomes based on the predicted value of the TUG test.

Clause 26. A non-transitory computer program product that causes a monitoring system to perform the steps executed by the monitoring system according to any of clauses 1 to 25.

Clause 27. A computer-readable medium having thereon computer-executable instructions, the computer-executable instructions upon execution configuring a monitoring system to perform the steps executed by the monitoring system according to any of clauses 1 to 25.

Although only a number of examples have been disclosed herein, other alternatives, modifications, uses and/or equivalents thereof are possible. Furthermore, all possible combinations of the described examples are also covered. Thus, the scope of the present disclosure should not be limited by particular examples, but should be determined only by a fair reading of the claims that follow. If reference signs related to drawings are placed in parentheses in a claim, they are solely for attempting to increase the intelligibility of the claim, and shall not be construed as limiting the scope of the claim.

The invention claimed is:

1. A system for assessing functional performance of an individual based on an analysis of a process of sitting down and standing up performed by the individual, the system comprising:
a sensor device, wherein the sensor device is a distributed pressure sensor, wherein the sensor device comprises an array of sensors of $N_r \times N_c$ that produces a $N_r \times N_c$ measurement matrix for each sampling time;

a monitoring system, connectable to the sensor device, configured to:
- receive signals coming from the sensor device, wherein received signals are in the form of a tri-dimensional tensor $T_S$ of order $N_r \times N_c \times N_S$, where $N_r$ is a number of rows of array of sensors, $N_c$ is the number of columns of array of sensors, and $N_S$ is a number of sampling times;
- pre-process the signals received from the sensor device, wherein pre-processing, by the monitoring system, the signals received from the sensor device comprises:
  - producing, by the monitoring system, an equi-order tensor $T_{MAX}$ of dimensions $N_r \times N_c \times N_{MAX}$;
  - vectoring the produced equi-order tensor $T_{MAX}$ into a vector V of length $N_{MAX}$, in which to each position i in is assigned a sum of the elements of the $N_r \times N_c$ measurement matrix in a position i of the tensor $T_{MAX}$;
- extract main features of the pre-processed signals as extracted predictor variables; and
- assess the functional performance of an individual based on the extracted predictor variables.

2. The system according to claim 1, wherein producing, by the monitoring system, the equi-order tensor $T_{MAX}$ of dimensions $N_r \times N_c \times N_{MAX}$ comprises:
- reformatting the tri-dimensional tensor $T_S$ of order $N_r \times N_c \times N_S$ according to:
  - if $N_S \geq N_{MAX}$, truncating a third dimension of the tensor $T_S$ to the length $N_{MAX}$, transforming the tri-dimensional tensor $T_S$ into the equi-order tensor $T_{MAX}$ of dimensions $N_r \times N_c \times N_{MAX}$;
  - if $N_S \geq N_{MAX}$, padding, by the monitoring system, the third dimension of the tri-dimensional tensor $T_S$ to the length $N_{MAX}$, transforming the tri-dimensional tensor $T_S$ into the equi-order tensor $T_{MAX}$ of dimensions $N_r \times N_c \times N_{MAX}$; and
  - if $N_S = N_{MAX}$, renaming the tri-dimensional tensor $T_S$ as the equi-order tensor $T_{MAX}$.

3. The system according to claim 2, wherein padding, by the monitoring system, the third dimension of the tri-dimensional tensor $T_S$ to the length $N_{MAX}$, if $N_S \geq N_{MAX}$, comprises:
- attaching after the tri-dimensional tensor $T_S$ of order $N_r \times N_c \times N_S$ a padding tensor $T_p$ of dimensions $N_r \times N_c \times N_p$, where $N_p$ is a padding length $N_p = N_{MAX} - N_S$.

4. The system according to claim 1, wherein the monitoring system extracts, the main features of the pre-processed signals to be used as the extracted predictor variables, the extracted predictor variables being signal descriptive variables in the time domain by:
- obtaining the signal descriptive variables in a time domain vector $V^{DESCRIPTIVE}$.

5. The system according to claim 4, wherein the signal descriptive variables in the time domain vector $V^{DESCRIPTIVE}$ are selected from at least one of the following:
- a range of signal variation;
- an instant of signal maximum peak;
- a signal standard deviation;
- a signal slope defined as a ratio between the range of signal variation and the instant of the signal maximum peak;
- a start time of signal change; and
- a signal integral.

6. The system according to claim 1, wherein pre-processing, by the monitoring system, the signals received from the sensor device comprises:
- correcting, by the monitoring system, the background of the vector V to obtain a background corrected vector $V_b$.

7. The system according to claim 6, wherein correcting, by the monitoring system, the background of the vector V comprises:
- subtracting from each element of the vector V the value of a minimum element of V, $V_{MIN}$ to obtain the background corrected vector $V_b$.

8. The system according to claim 7, wherein the monitoring system extracts the main features of the pre-processed signals to be used as the extracted predictor variables, the extracted predictor variables being signal time series variables in the time domain by:
- filtering the noise of the background corrected vector with a smoothing moving window to obtain a filtered background corrected vector; and
- reducing, by the monitoring system, a sample length of the filtered background corrected vector by a decimation factor of d, to obtain the signal time series variables in a time domain vector $V^{TIME}$.

9. The system according to claim 8, wherein reducing, by the monitoring system, the sample length of the filtered background corrected vector by the decimation factor of d comprises the following:
- applying a simple resampling of the filtered background corrected vector at each time d;
- applying a lowpass Chebyshev Type I Infinite Impulse Response (IIR) filter; and
- applying a Finite Impulse Response (FIR) filter with a Hamming window.

10. The system according to claim 8, wherein the monitoring system extracts the main features of the pre-processed signals to be used as the extracted predictor variables, the extracted predictor variables being signal spectral variables in the frequency domain by:
- truncating the background corrected vector $V_b$ length to a floor operator $L_T$ of maximum power of 2 of the length of the background corrected vector $V_b$ to obtain a truncated background corrected vector;
- applying a Fast Fourier transform to the truncated background corrected vector using a Discrete Fast Fourier method;
- obtaining the spectral power P of the background corrected vector $V_b$ based on the result of applying the Fast Fourier transform to the truncated background corrected vector; and
- truncating the obtained spectral power P to obtain the extracted predictor variables as signal spectral variables in a frequency domain vector $V^{FREQUENCY}$ is obtained.

11. The system according to claim 10, wherein the monitoring system extracts the main features of the pre-processed signals to be used as the extracted predictor variables by:
- obtaining the respective maximum and minimum values of the extracted predictor variables in one or more of the vectors $V^{DESCRIPTIVE}$, $V^{TIME}$ and/or $V^{FREQUENCY}$,
- normalizing, based on the obtained maximum and minimum values, between 0 and 1, the extracted predictor variables in one or more of the vectors $V^{DESCRIPTIVE}$, $V^{TIME}$ and/or $V^{FREQUENCY}$ to obtain normalized extracted predictor variables;
- attaching in a vector $V^P$ the normalized extracted predictor variables.

12. The system according to claim 1, wherein assessing, by the monitoring system, the functional performance of an individual based on the extracted predictor variables comprises:
- predicting a value of a TUG (Timed Up Go) test of the individual based on the extracted predictor variables; and
- assessing the functional performance of an individual based on the predicted value of the TUG test.

13. The system according to claim 1, wherein the monitoring system assesses the functional performance of an individual based on the extracted predictor variables by:
- identifying a state of fragility or robustness of the individual based on the extracted predictor variables.

14. The system according to claim 1, wherein the monitoring system assesses the functional performance of an individual based on the extracted predictor variables by:
- identifying individuals with high risk of fractures and other health related adverse outcomes based on the extracted predictor variables.

* * * * *